(12) United States Patent
Atkinson et al.

(10) Patent No.: US 8,633,319 B2
(45) Date of Patent: Jan. 21, 2014

(54) 7-(1H-PYRAZOL-4-YL)-1,6-NAPHTHYRIDINE COMPOUNDS AS SYK INHIBITORS

(75) Inventors: Francis Louis Atkinson, Stevenage (GB); Michael David Barker, Stevenage (GB); Clement Douault, Stevenage (GB); Neil Stuart Garton, Stevenage (GB); John Liddle, Stevenage (GB); Vipulkumar Kantibhai Patel, Stevenage (GB); Alexander George Steven Preston, Stevenage (GB); David Matthew Wilson, Stevenage (GB)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 13/642,338

(22) PCT Filed: Apr. 27, 2011

(86) PCT No.: PCT/EP2011/056600
§ 371 (c)(1),
(2), (4) Date: Oct. 19, 2012

(87) PCT Pub. No.: WO2011/134971
PCT Pub. Date: Nov. 3, 2011

(65) Prior Publication Data
US 2013/0040984 A1    Feb. 14, 2013

(30) Foreign Application Priority Data

Apr. 29, 2010    (GB) .................................. 1007203.1

(51) Int. Cl.
*C07D 471/04*    (2006.01)
*A61K 31/4375*    (2006.01)

(52) U.S. Cl.
USPC ......................................... 546/122; 514/300

(58) Field of Classification Search
None
See application file for complete search history.

(56) References Cited

FOREIGN PATENT DOCUMENTS

| WO | 02/26712 | 4/2002 |
|---|---|---|
| WO | 03/057695 | 7/2003 |
| WO | 2004/035604 | 4/2004 |
| WO | 2006/038594 | 4/2006 |
| WO | 2009/026717 | 3/2009 |
| WO | 2010/015518 | 2/2010 |
| WO | 2010/015520 | 2/2010 |
| WO | 2010/048149 | 4/2010 |
| WO | 2010/070076 | 4/2010 |
| WO | 2010/120935 | 10/2010 |

OTHER PUBLICATIONS

Morales-Torres; "The status of fostamatinib in the treatment of rheumatoid arthritis"; 2012; Expert. Rev. Clin. Immunol.; 8(7):609-15; PubMed abstract; PMID: 23078058.*

Saini et al.; "Cultured peripheral blood mast cells from chronic idiopathic urticarial patients spontaneously degranulate upon IgE sensitization: Relationship to expression of Syk and SHIP-2"; 2009; Clinical Immunology; 132: 342-348.*
Cheng et al.; Syk Tyrosine Kinase Required for Mouse Viability and B-cell Development; Nature; 1995; 378; 303-306.
Cywin et al.; Discovery and SAR of Novel [1,6]Naphthyridines as Potent Inhibitors of Spleen Tyrosine Kinase (SYK); Bioorganic & Medicinal Chemistry Letters; 2003; 13; 1415-1418.
Edwards et al.; Efficacy of B-Cell-Targeted Therapy with Rituximab in Patients with Rheumatoid Arthritis; The New England Journal of Medicine; 2004; 350(25); 2572-2581.
Friedberg et al.; Inhibition of Syk with fostamatinib disodium has signifcant clinical activity in non-Hodgkin lymphona and chronic lymphocytic leukemia; Blood; 2010; 115(13); 2578-2585.
Gururajan et al.; Spleen Tyrosine Kinase (Syk), a Novel Target of Curcumin, Is Required for B Lymphoma Growth1; The Journal of Immunology; 2007; 178(1); 111-121.
Kurosaki et al.; Regulation of the Phospholipase C-y2 Pathway in B Cells; Immunological Reviews; 2000; 176(1); 19-29.
Leseux et al.; Syk-Dependent mTOR Activation in Follicular Lymphoma Cells; Blood; 2006; 108(13); 4156-4162.
Meltzer et al.; An Intranasal Syk-Kinase Inhibitor (R112) Improves the Symptoms of Seasonal Allergic Rhinitis in a Park Environment; Journal of Allergy and Clinical Immunology; 2005; 115; 791-796.
Turner et al.; Perinatal Lethality and Blocked B-Cell Development in Mice Lacking the Tyrosine Kinase Syk; Nature; 1995; 378(6554); 298-302.
Vonakis et al.; New Concepts in Chronic Urticaria; Current Opinion in Immunology; 2008; 20; 709-716.

(Continued)

*Primary Examiner* — Timothy Thomas
(74) *Attorney, Agent, or Firm* — Kathryn L. Coulter

(57) ABSTRACT

The present invention relates to a compound of formula (I):

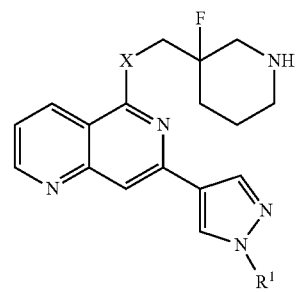

or a salt thereof;
which is an inhibitor of spleen tyrosine kinase (Syk) and therefore potentially of use in treating diseases resulting from inappropriate activation of mast and/or basophil cells, macrophages, and B-cells and related inflammatory responses and tissue damage, for instance inflammatory disease and/or allergic disorders, and in cancer therapy, specifically heme malignancies, chronic spontaneous urticaria and autoimmune conditions.

11 Claims, No Drawings

(56) References Cited

OTHER PUBLICATIONS

Weinblatt et al.; Treatment of Rheumatoid Arthritis with a Syk Kinase Inhibitor; Arthritis & Rheumatism; 2008; 58(11); 3309-3318.

Wong et al.; Targeting Syk as a Treatment for Allergic and Autoimmune Disorders; Expert Opinion on Investigational Drugs; 2004; 13(7); 743-762.

* cited by examiner

7-(1H-PYRAZOL-4-YL)-1,6-NAPHTHYRIDINE COMPOUNDS AS SYK INHIBITORS

This application is filed pursuant to 35 U.S.C. §371 as a United States National Phase Application of International Patent Application No. PCT/EP2011/056600 filed on Apr. 27, 2011, which claims priority from Great Britain Application No. 1007203.1 filed in the United Kingdom on Apr. 29, 2010.

The present invention relates to novel chemical compounds which have activity against the spleen tyrosine kinase (Syk), processes for their preparation, pharmaceutically acceptable formulations containing them and their use in therapy.

Syk is a non-receptor tyrosine kinase that is involved in coupling activated immunoreceptors to signal downstream events that mediate diverse cellular responses, including proliferation, differentiation, and phagocytosis. Syk is widely expressed in hematopoietic cells. Syk inhibitors have potential anti-inflammatory and immunomodulating activities. They inhibit Syk-mediated IgG Fc epsilon and gamma receptor and BCR receptor signaling, resulting in inhibition of the activation of mast cells, macrophages, and B-cells and related inflammatory responses and tissue damage. Accordingly, Syk inhibitors have attracted interest in a number of therapeutic areas, including the treatment of rheumatoid arthritis, B-cell lymphoma and asthma/rhinitis.

Rheumatoid arthritis (RA) is an auto-immune disease affecting approximately 1% of the population. It is characterised by inflammation of articular joints leading to debilitating destruction of bone and cartilage. Recent clinical studies with rituximab, which causes a reversible B cell depletion, (J. C. W. Edwards et al. New Eng. J. Med., 2004, 350, 25: 2572-2581), have shown that targeting B cell function is an appropriate therapeutic strategy in auto-immune diseases such as RA. Clinical benefit correlates with a reduction in auto-reactive antibodies (or rheumatoid factor) and these studies suggest that B cell function and indeed auto-antibody production are central to the ongoing pathology in the disease.

Studies using cells from mice deficient in the Syk have demonstrated a non-redundant role of this kinase in B cell function. The deficiency in Syk is characterised by a block in B cell development (M. Turner et al. Nature, 1995, 378: 298-302 and Cheng et al. Nature, 1995, 378: 303-306). These studies, along with studies on mature B cells deficient in Syk (Kurosaki et al. Immunol. Rev. 2000, 176:19-29), demonstrate that Syk is required for the differentiation and activation of B cells. Hence, inhibition of Syk in RA patients is likely to block B cell function and hence to reduce rheumatoid factor production. In addition to the role of Syk in B cell function, of relevance to the treatment of RA, is the requirement for Syk activity in Fc receptor (FcR) signalling. FcR activation by immune complexes in RA has been suggested to contribute to the release of multiple pro-inflammatory mediators.

The contribution of Syk dependent processes to the pathology of RA has been reviewed by Wong et al. (Expert Opinion Investigational Drugs, 2004, 13 (7): 743-762).

The results of a 12 week clinical trial for the Syk inhibitor R788 (fostamatinib disodium, Rigel) have been published: Treatment of rheumatoid arthritis with a syk kinase inhibitor: A twelve-week, randomized, placebo-controlled trial, Arthritis & Rheumatism, 58(11), 2008: 3309-3318.

Syk inhibitors may also be useful in cancer therapy, specifically heme malignancies, particularly Non-Hodgkin's Lymphomas including follicular (FL), mantle cell, Burkitt and diffuse large B cell (DLBCL) lymphomas.

Studies have shown that Syk is dysregulated by overexpression and/or constitutively activation in a variety of primary B-lymphoma tumors and also in B-lymphoma cell lines. Syk, through the PI3K/AKT pathway, the PLD pathway and AKT independent signalling, activates mTOR (mammalian target of rapamycin) which in turn increases B-cell survival and proliferation. Inhibition of Syk, in vitro, results in decreased mTOR activation and a reduction of clonicity in FL cells. Inhibition of Syk kinase with curcumin in a murine model of B lymphoma (BKS-2) gave a significant reduction of tumour burden as measured by the total splenocyte number (Leseux L. et al. Blood 15 Dec. 2006, 108(13): 4156-4162 and Gururajan M. et al. Journal of Immunology, 2007, 178: 111-121).

Results of a Phase 2 clinical trial of R788 (fostamatinib disodium) in patients with relapsed or refractory B-Cell non-Hodgkin's lymphoma (NHL) show that the compound is well-tolerated by these patients, as well as a therapeutic benefit in patients suffering from diffuse large B-Cell lymphoma (DLBCL) and chronic lymphocytic leukemia/small lymphocytic lymphoma (CLL/SLL). Despite the fact that the patients enrolled in this trial had advanced disease and had failed treatment with marketed therapies, a significant number of them were particularly responsive to Syk inhibition with R788 (www.Rigel.com; Friedberg J. W. et al. Blood, 1 Apr. 2010; 115(13): 2578-85).

Syk inhibitors may also be useful in the treatment of asthma and rhinitis as they are important in transducing the downstream cellular signals associated with cross-linking FcεR1 and/or FcγR1 receptors, and they are positioned early in the signalling cascade. In mast cells, for example, the early sequence of FcεR1 signalling following allergen cross-linking of receptor-IgE complexes involves first Lyn (a Src family tyrosine kinase) and then Syk.

Allergic rhinitis and asthma are diseases associated with hypersensitivity reactions and inflammatory events involving a multitude of cell types including mast cells, eosinophils, T cells and dendritic cells. Following exposure to allergen, high affinity immunoglobulin receptors for IgE (FcεRI) and IgG (FcγRI) become cross-linked and activate downstream processes in mast cells and other cell types leading to the release of pro-inflammatory mediators and airway spasmogens. In the mast cell, for example, IgE receptor cross-linking by allergen leads to release of mediators including histamine from pre-formed granules, as well as the synthesis and release of newly synthesised lipid mediators including prostaglandins and leukotrienes.

The Syk inhibitor R112 (Rigel), dosed intranasally in a phase I/II study for the treatment of allergic rhinitis, was shown to give a statistically significant decrease in $PGD_2$, a key immune mediator that is highly correlated with improvements in allergic rhinorrhea, as well as being safe across a range of indicators, thus providing the first evidence for the clinical safety and efficacy of a topical Syk inhibitor (see Meltzer E. O. et al. "An intranasal Syk kinase inhibitor (R112) improves the symptoms of seasonal allergic rhinitis in a park environment"; Journal of Allergy and Clinical Immunology, 2005, 115(4): 791-796). In a further phase II clinical trial, for allergic rhinitis, R112 was however shown as having a lack of efficacy versus placebo (www.clinicaltrials.gov Identifier NCT0015089).

Acute and chronic urticaria are common skin diseases thought to affect around 25% of the total population within the USA (see "New concepts in chronic urticaria"; Current Opinions in Immunology, 2008, 20: 709-716). Although urticaria can be triggered by allergic reactions many cases have an unclear etiology. Chronic spontaneous urticaria is defined as when wide spread wheals are present for greater than 6 weeks. There are many pathological similarities in chronic urticaria patients, in terms of extent of wheals in the skin, with allergen-induced mast and basophil cell degranulation reactions via IgE activation. Around 40% of chronic spontaneous urticaria patients contain serum IgG auto-antibodies targeting IgE or the IgE receptor (Fc Epsilon Receptor) and these are thought to drive the histamine and other mediator release via mast and basophil degranulation. Syk inhibitors would inhibit the signalling response post IgE mediated Fc Epsilon activation and inhibit the mediator release known to be involved in chronic pruritis in multiple diseases.

WO03/057695A1 (Boehringer Ingelheim Pharmaceuticals, Inc.) describes novel 1,6-naphthyridines that have Syk inhibitory activity. These are further described in "Discovery and SAR of Novel [1,6] Naphthyridines as Potent Inhibitors of Spleen Tyrosine Kinase (SYK)" (Bioorganic & Medicinal Chemistry Letters 13 (2003): 1415-1418). This has been followed with two more recent patent applications, WO2010/015518A2 and WO2010/015520A1 (Boehringer Ingelheim International GmbH), describing 4-dimethylamino-phenyl-substituted naphthyridines and substituted naphthyridines, respectively.

WO04/035604A2 (Millennium Pharmaceuticals, Inc.) discloses the structural co-ordinates of the human Syk protein.

There remains however the need to identify further compounds which are inhibitors of spleen tyrosine kinase (Syk).

Thus, in a first aspect invention, the present invention provides a compound of formula (I):

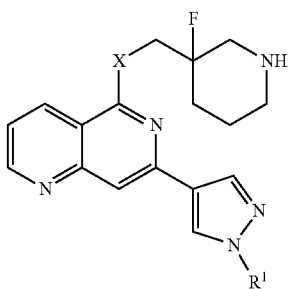

(I)

wherein:
X is O or NH;
$R^1$ is $C_{2-4}$ alkyl, $C_{3-7}$cycloalkyl, hydroxy$C_{2-4}$ alkyl, $C_{1-2}$ alkoxy$C_{1-4}$alkyl, trifluoromethyl$C_{1-2}$ alkyl or benzyl;
or a salt thereof (hereinafter "compounds of the invention").

In one aspect, X is NH.

In one embodiment $R^1$ is ethyl, iso-propyl, t-butyl, cyclopentyl, methoxymethyl, methoxyethyl, hydroxyethyl, 2,2-hydroxymethylpropyl, 2,2,2-trifluoroethyl or benzyl. In another embodiment, $R^1$ is $C_{2-4}$alkyl, $C_{3-7}$cycloalkyl or $C_{1-2}$alkoxy$C_{1-4}$alkyl. In another embodiment, $R^1$ is ethyl, t-butyl, —CH$_2$OCH$_3$, —CH$_2$C(CH$_3$)$_2$OH, —CH$_2$CH$_2$OH, —CH$_2$CH$_2$OCH$_3$, —CH(CH$_3$)$_2$, —CH$_2$CF$_3$, benzyl or cyclopentyl. In another embodiment, $R^1$ is ethyl, t-butyl, or methoxymethyl. In another embodiment, $R^1$ is ethyl or t-butyl. In a further embodiment, $R^1$ is t-butyl.

It is to be understood that the present invention covers all combinations of substituent groups described hereinabove.

It will be appreciated that the compounds of formula (I) comprise a chiral centre at the 3-carbon of the piperidinyl ring. It has been found that those having the S absolute stereochemistry are generally preferred, on account of better drug development properties, including better bioavailability (as measured in predictive animal pharmacokinetic studies) and lesser hERG activity.

Accordingly, in one embodiment, the present invention provides a compound of formula (I) having the S absolute stereochemistry. In another embodiment, the present invention provides a compound of formula (I) having the S absolute stereochemistry, that is a compound of formula (II):

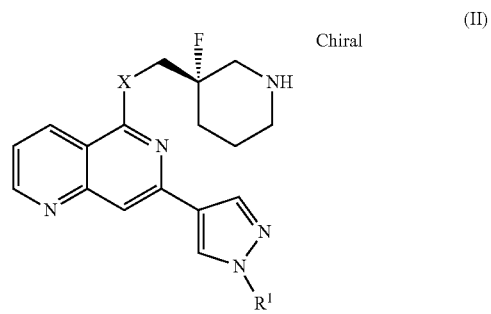

(II)

wherein:
X and $R^1$ are as hereinbefore defined;
or a salt thereof.

Compounds of the invention include the compounds of Examples 1 to 11 and salts thereof.

In one embodiment, the present invention provides a compound formula (I) selected from the group consisting of:
7-(1-ethyl-1H-pyrazol-4-yl)-N-{[(3S)-3-fluoro-3-piperidinyl]methyl}-1,6-naphthyridin-5-amine;
7-[1-(1,1-dimethylethyl)-1H-pyrazol-4-yl]-N-{[(3S)-3-fluoro-3-piperidinyl]methyl}-1,6-naphthyridin-5-amine;
N-{[(3S)-3-fluoro-3-piperidinyl]methyl}-7-{1-[(methyloxy)methyl]-1H-pyrazol-4-yl}-1,6-naphthyridin-5-amine;
7-(1-ethyl-1H-pyrazol-4-yl)-5-({[(3S)-3-fluoro-3-piperidinyl]methyl}oxy)-1,6-naphthyridine;
1-{4-[5-({[(3S)-3-fluoro-3-piperidinyl]methyl}amino)-1,6-naphthyridin-7-yl]-1H-pyrazol-1-yl}-2-methyl-2-propanol;
2-{4-[5-({[(3S)-3-fluoro-3-piperidinyl]methyl}amino)-1,6-naphthyridin-7-yl]-1H-pyrazol-1-yl}ethanol;
N-{[(3S)-3-fluoro-3-piperidinyl]methyl}-7-{1-[2-(methyloxy)ethyl]-1H-pyrazol-4-yl}-1,6-naphthyridin-5-amine;
7-(1-cyclopentyl-1H-pyrazol-4-yl)-N-[(3-fluoro-3-piperidinyl)methyl]-1,6-naphthyridin-5-amine;
N-[(3-fluoro-3-piperidinyl)methyl]-7-[1-(2,2,2-trifluoroethyl)-1H-pyrazol-4-yl]-1,6-naphthyridin-5-amine;
N-{[(3S)-3-fluoro-3-piperidinyl]methyl}-7-[1-(2,2,2-trifluoroethyl)-1H-pyrazol-4-yl]-1,6-naphthyridin-5-amine;
N-{[(3R)-3-fluoro-3-piperidinyl]methyl}-7-[1-(2,2,2-trifluoroethyl)-1H-pyrazol-4-yl]-1,6-naphthyridin-5-amine;
N-[(3-fluoro-3-piperidinyl)methyl]-7-[1-(phenylmethyl)-1H-pyrazol-4-yl]-1,6-naphthyridin-5-amine;
N-{[3-fluoro-3-piperidinyl]methyl}-7-[1-(1-methylethyl)-1H-pyrazol-4-yl]-1,6-naphthyridin-5-amine;
N-{[(3S)-3-fluoro-3-piperidinyl]methyl}-7-[1-(1-methylethyl)-1H-pyrazol-4-yl]-1,6-naphthyridin-5-amine; and
N-{[(3R)-3-fluoro-3-piperidinyl]methyl}-7-[1-(1-methylethyl)-1H-pyrazol-4-yl]-1,6-naphthyridin-5-amine; and
salts thereof.

In another embodiment, the present invention provides a compound formula (I) selected from the group consisting of:
7-(1-ethyl-1H-pyrazol-4-yl)-N-{[(3S)-3-fluoro-3-piperidinyl]methyl}-1,6-naphthyridin-5-amine;
7-[1-(1,1-dimethylethyl)-1H-pyrazol-4-yl]-N-{[(3S)-3-fluoro-3-piperidinyl]methyl}-1,6-naphthyridin-5-amine;
N-{[(3S)-3-fluoro-3-piperidinyl]methyl}-7-{1-[(methyloxy)methyl]-1H-pyrazol-4-yl}-1,6-naphthyridin-5-amine;

7-(1-ethyl-1H-pyrazol-4-yl)-5-({[(3S)-3-fluoro-3-piperidinyl]methyl}oxy)-1,6-naphthyridine;
1-{4-[5-({[(3S)-3-fluoro-3-piperidinyl]methyl}amino)-1,6-naphthyridin-7-yl]-1H-pyrazol-1-yl}-2-methyl-2-propanol;
2-{4-[5-({[(3S)-3-fluoro-3-piperidinyl]methyl}amino)-1,6-naphthyridin-7-yl]-1H-pyrazol-1-yl}ethanol;
N-{[(3S)-3-fluoro-3-piperidinyl]methyl}-7-{1-[2-(methyloxy)ethyl]-1H-pyrazol-4-yl}-1,6-naphthyridin-5-amine;
7-(1-cyclopentyl-1H-pyrazol-4-yl)-N-[(3-fluoro-3-piperidinyl)methyl]-1,6-naphthyridin-5-amine;
N-[(3-fluoro-3-piperidinyl)methyl]-7-[1-(2,2,2-trifluoroethyl)-1H-pyrazol-4-yl]-1,6-naphthyridin-5-amine; and
N-[(3-fluoro-3-piperidinyl)methyl]-7-[1-(phenylmethyl)-1H-pyrazol-4-yl]-1,6-naphthyridin-5-amine; and
salts thereof.

In another embodiment, the present invention provides a compound formula (I) selected from the group consisting of:
7-(1-ethyl-1H-pyrazol-4-yl)-N-{[(3S)-3-fluoro-3-piperidinyl]methyl}-1,6-naphthyridin-5-amine; and
7-[1-(1,1-dimethylethyl)-1H-pyrazol-4-yl]-N-{[(3S)-3-fluoro-3-piperidinyl]methyl}-1,6-naphthyridin-5-amine; and
salts thereof.

In another embodiment, the present invention provides a compound formula (I) which is 7-[1-(1,1-dimethylethyl)-1H-pyrazol-4-yl]-N-{[3-fluoro-3-piperidinyl]methyl}-1,6-naphthyridin-5-amine

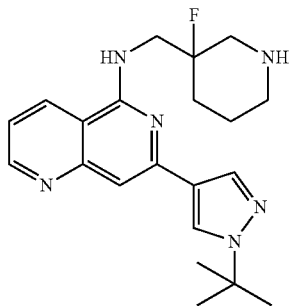 [SMILES: CC(C)(C)n1cc(-c2cc3ncccc3c(NCC3(F)CCCNC3)n2)cn1]

or a salt thereof.

In a further embodiment, the present invention provides a compound formula (I) which is 7-[1-(1,1-dimethylethyl)-1H-pyrazol-4-yl]-N-{[(3S)-3-fluoro-3-piperidinyl]methyl}-1,6-naphthyridin-5-amine

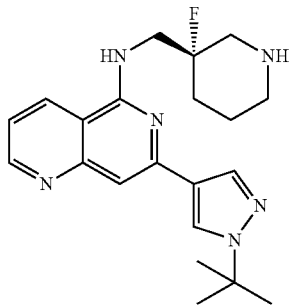 [SMILES: CC(C)(C)n1cc(-c2cc3ncccc3c(NC[C@]3(F)CCCNC3)n2)cn1]

or a salt thereof.

Included within the scope of the "compounds of the invention" are all solvates (including hydrates), complexes, polymorphs, prodrugs, radiolabelled derivatives, stereoisomers and optical isomers of the compounds of formula (I) and salts thereof.

It is to be understood that the references herein to compounds of formula (I) and salts thereof covers the compounds of formula (I) as free bases, or as salts thereof, for example as pharmaceutically acceptable salts thereof. Thus, in one embodiment, the invention is directed to compounds of formula (I) as the free base. In another embodiment, the invention is directed to compounds of formula (I) and salts thereof. In a further embodiment, the invention is directed to compounds of formula (I) and pharmaceutically acceptable salts thereof.

Compounds of the present invention are useful as inhibitors of Syk. Compounds of the present invention exhibit low activity in the hERG binding assay, a key measure of potential cardiac toxicity. Compounds of the present invention are also negative in the Bacterial Reverse Mutation Test, an assay designed to detect a wide range of chemical substances that can produce genetic damage that leads to gene mutations (base pair substitutions and frameshift mutations).

Compounds of the present invention are thus potentially of use in treating some cancer therapies, in particular heme malignancies, as well as inflammatory conditions which involve B cells and/or activated macrophages, and also diseases resulting from inappropriate mast cell activation, for instance allergic and inflammatory diseases.

When used herein, the term "alkyl" includes all saturated straight chain and branched isomers. For example, $C_{1-4}$alkyl means a straight or branched chain alkyl group containing at least 1, and at most 4, carbon atoms. Representative examples thereof include, but are not limited to, methyl, ethyl, n-propyl, iso-propyl, n-butyl, sec-butyl, iso-butyl and t-butyl.

When used herein, the term "alkoxy" includes all saturated straight chain and branched isomers. For example, $C_{1-2}$alkoxy means a straight chain alkoxy group containing at least 1, and at most 2, carbon atoms. Representative examples of "alkoxy" as used herein include, but are not limited to, methoxy and ethoxy.

When used herein the term "cycloalkyl" includes, unless otherwise defined, carbocyclic rings having from three to seven ring carbon atoms. Representative examples thereof include, but are not limited to, cyclopropyl, cyclobutyl, cyclopentyl, cyclohexyl and cycloheptyl. Preferably the cycloalkyl ring comprises five or six ring carbon atoms.

When used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio. The skilled artisan will appreciate that pharmaceutically acceptable salts of the compound of the present invention may be prepared.

When used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form with a suitable base or acid, respectively. Indeed, in certain embodiments of the invention, pharmaceutically acceptable salts may be preferred over the respective free base or free acid because such salts impart greater stability or solubility to the molecule thereby facilitating formulation into a dosage form.

The compounds of formula (I) are basic and accordingly generally capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate. In one embodiment, the present invention provides a pharmaceutically acceptable salt of a compound of formula (I) which is the hydrochloride salt.

The compounds of formula (I) contain a chiral centre and, therefore, exist as individual enantiomers, or as mixtures thereof. Where the stereochemistry of the chiral centre is not specified the structure is intended to encompass each enantiomer and all mixtures thereof. Thus, the compounds of formula (I) may be used as racemic modifications including racemic mixtures and racemates, enantiomerically enriched mixtures, or as enantiomerically pure individual stereoisomers. The present invention includes all such mixtures as well as pure individual enantiomers. Generally it is preferred to use a compound of formula (I) in the form of a purified single enantiomer, for instance a compound of formula (II).

The individual enantiomers of a compound of formula (I) may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled person will appreciate that where the desired stereoisomer is converted into another chemical entity by one of the separation procedures described above, a further step is required to liberate the desired form. Alternatively, specific enantiomers may be synthesized by asymmetric synthesis using optically active reagents, substrates, catalysts or solvents, or by converting one enantiomer to the other by asymmetric transformation.

A compound of the present invention may exist in solid or liquid form. In the solid state, the compound of the present invention may exist in crystalline or non-crystalline (amorphous) form, or as a mixture thereof. For a compound of the present invention that is in crystalline form, the skilled artisan will appreciate that pharmaceutically acceptable solvates may be formed wherein solvent molecules are incorporated into the crystalline lattice during crystallization. Solvates may involve non-aqueous solvents such as, but not limited to, ethanol, isopropanol, n-butanol, i-butanol, acetone, tetrahydrofuran, dioxane, DMSO, acetic acid, ethanolamine, and ethyl acetate, or they may involve water as the solvent that is incorporated into the crystalline lattice. Solvates wherein water is the solvent incorporated into the crystalline lattice are typically referred to as "hydrates". Hydrates include stoichiometric hydrates as well as compositions containing variable amounts of water. The invention includes all such solvates. Further, the term solvate encompasses solvates of both the free base compound as well as any salt thereof.

The skilled artisan will further appreciate that a compound of the present invention that exists in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

A compound of formula (I) may be prepared by the general synthetic schemes described hereinafter.

Scheme 1: Synthesis of 1,1-dimethylethyl (3R)-3-(aminomethyl)-3-fluoro-1-piperidinecarboxylate

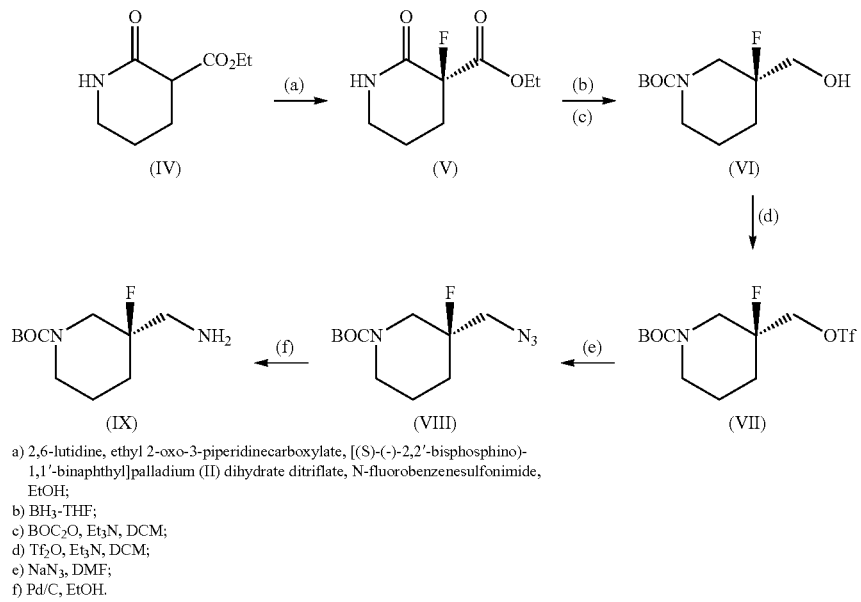

a) 2,6-lutidine, ethyl 2-oxo-3-piperidinecarboxylate, [(S)-(-)-2,2'-bisphosphino)-1,1'-binaphthyl]palladium (II) dihydrate ditriflate, N-fluorobenzenesulfonimide, EtOH;
b) BH₃-THF;
c) BOC₂O, Et₃N, DCM;
d) Tf₂O, Et₃N, DCM;
e) NaN₃, DMF;
f) Pd/C, EtOH.

Scheme 2: Synthesis of 1-(1,1-dimethylethyl)-4-(4,4,5,5-tetramethyl-1,3,2-dioxaborolan-2-yl)-1H-pyrazole
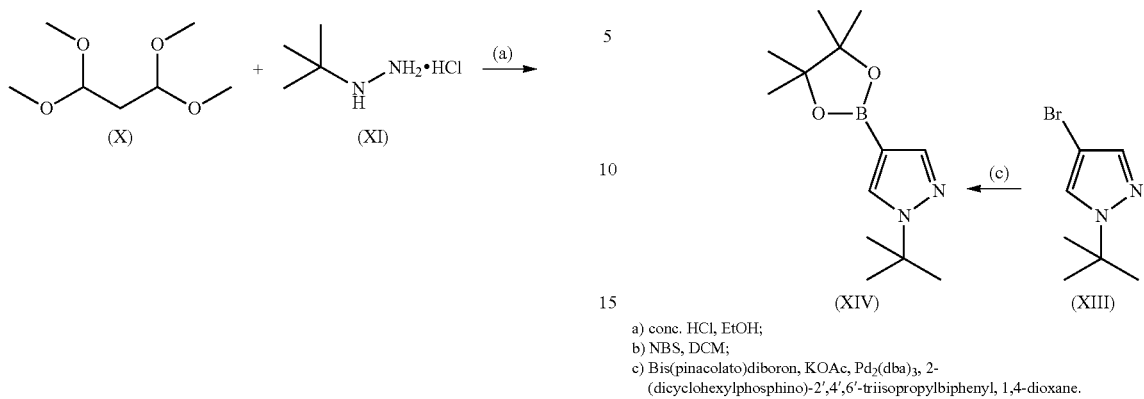
a) conc. HCl, EtOH;
b) NBS, DCM;
c) Bis(pinacolato)diboron, KOAc, Pd$_2$(dba)$_3$, 2-(dicyclohexylphosphino)-2′,4′,6′-triisopropylbiphenyl, 1,4-dioxane.
Scheme 3: Synthesis of 1-[(methyloxy)methyl]-4-(4,4,5,5-tetramethyl-1,3,2-dioxaborolan-2-yl)-1H-pyrazole
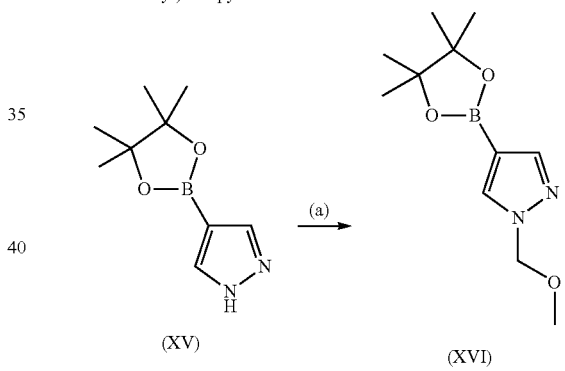
a) Iodomethyl methyl ether, K$_2$CO$_3$, acetonitrile.
Scheme 4 (X = NH)
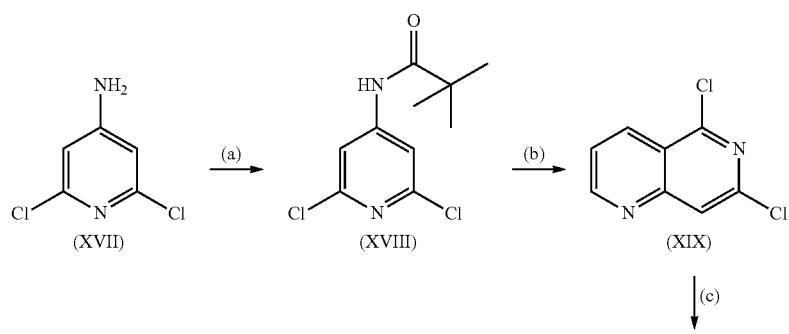

-continued

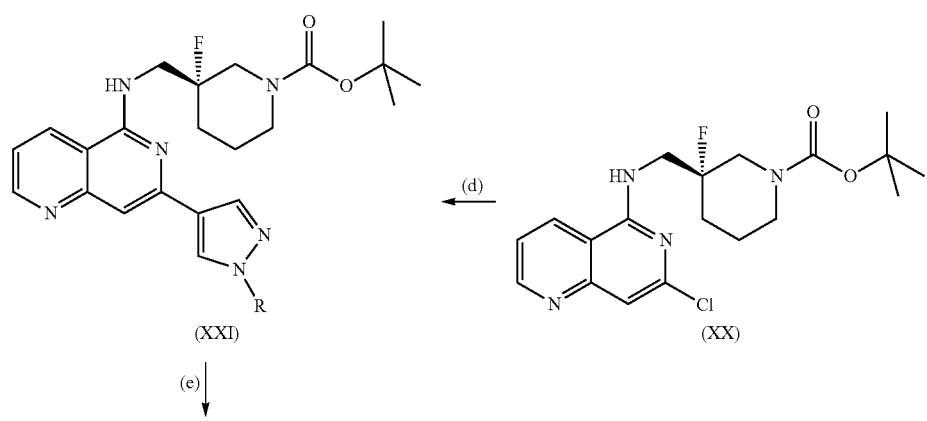

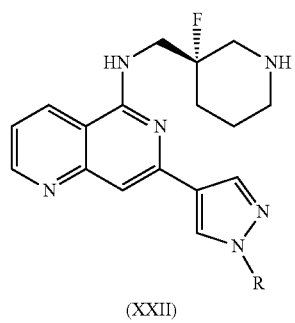

Where R = Et, t-Bu, CH₂OMe
a) 2,6-dichloro-4-pyridinamine, 2,2-dimethylpropanoyl chloride, Et₃N, DCM
b) nBuLi, (2E)-3-(dimethylamino)-2-propenal, THF;
c) 1,1-dimethylethyl (3R)-3-(aminomethyl)-3-fluoro-1-piperidinecarboxylate (see scheme 1), DIPEA, NMP;
d) Pyrazole boronic ester, Cs₂CO₃, Pd(PPh₃)₄, 1,4-dioxane, H₂O; or pyrazole boronic ester, KOH, PEPPSI cat., DME, EtOH, H₂O;
e) TFA, DCM.

Scheme 5 (X = O): Synthesis of 7-(1-ethyl-1H-pyrazol-4-yl)-5-({[(3S)-3-fluoro-3-piperidinyl]methyl}oxy)-1,6-naphthyridine

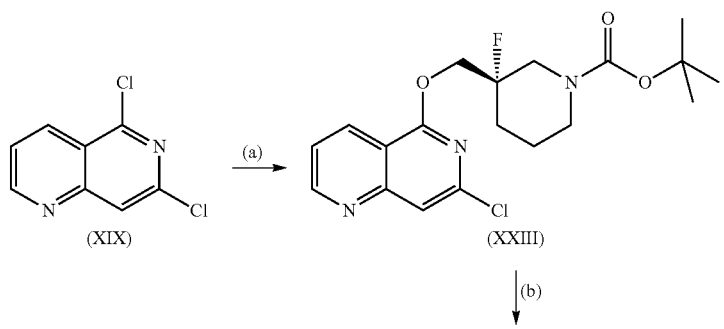

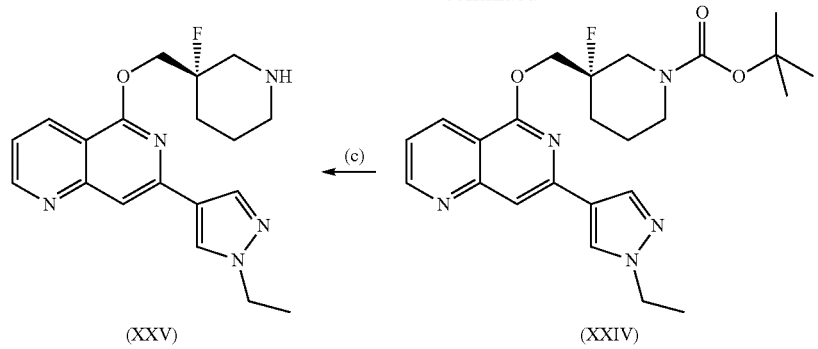
(XXV) (XXIV)
a) 1,1-dimethylethyl (3S)-fluoro-3-(hydroxymethyl)-1-piperidinecarboxylate (see scheme 1), NaH, DMF;
b) 1-ethyl-4-(4,4,5,5-tetramethyl-1,3,2-dioxaborolan-2-yl)-1H-pyrazole, $Cs_2CO_3$, $Pd(PPh_3)_4$, 1,4-dioxane, $H_2O$;
c) TFA, DCM.
Scheme 6: Synthesis of 7-[1-(1,1-dimethylethyl)-1H-pyrazol-4-yl]-N-{[(3S)-3-fluoro-3-piperidinyl]methyl}-1,6-naphthyridin-5-amine
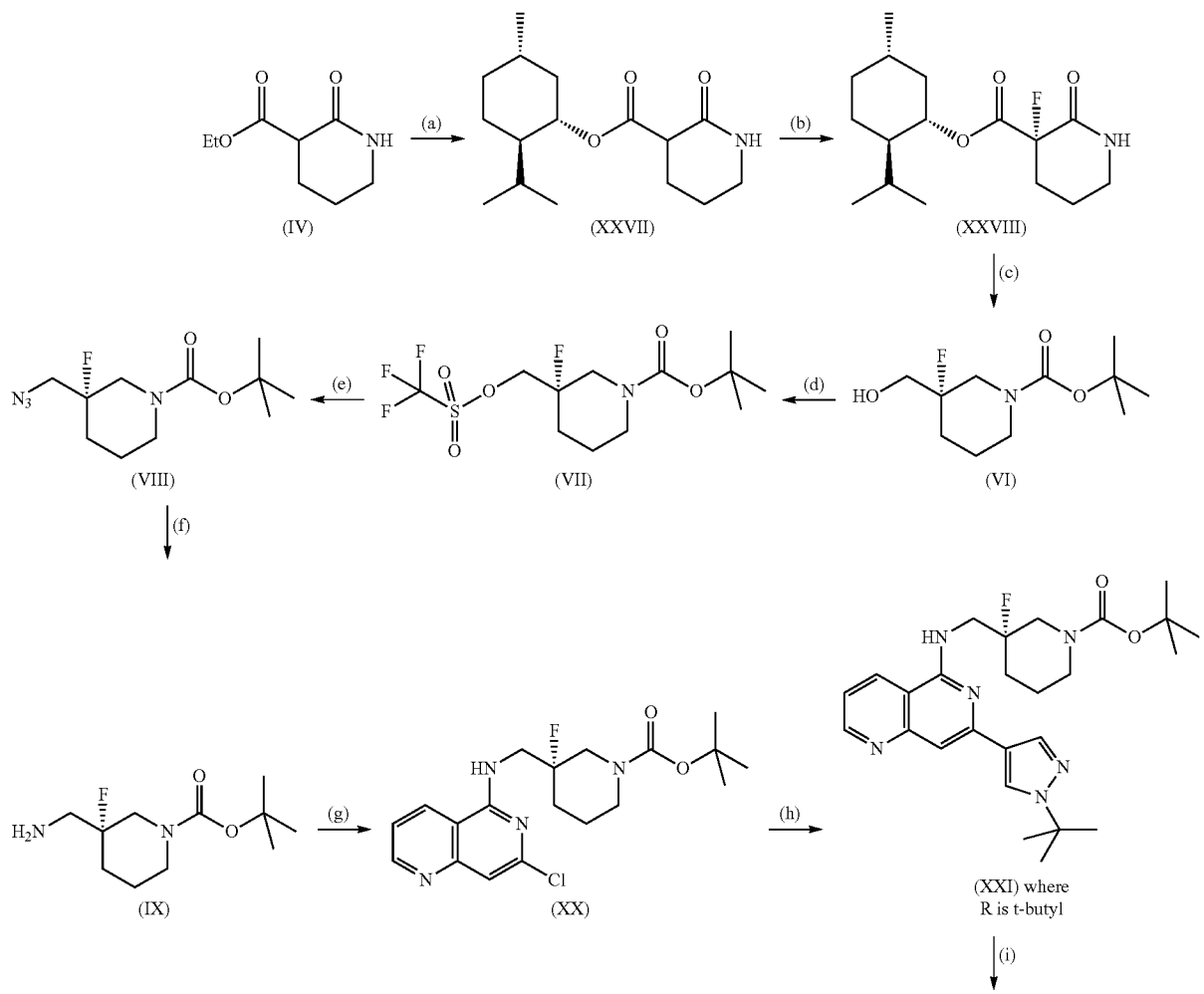

-continued

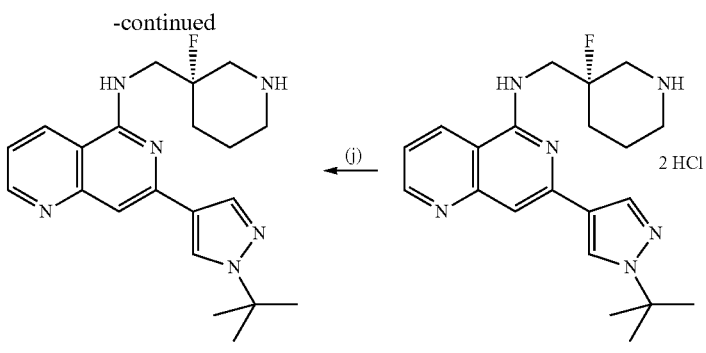

Example 2 (free base)     Example 2 (HCl salt)

a) (+)-Menthol, DMAP, toluene, reflux;
b) [(S)BINAP]Pd(OTf)$_2$; (PhSO$_2$)$_2$NF; 2,6-lutidine; EtOH;
c) (i) BH$_3$•DMS; THF; reflux;
   (ii) Boc$_2$O;
d) Tf$_2$O, pyridine;
e) NaN$_3$, DMF;
f) Pt/C, hydrogen, THF, NH$_3$(aq);
g) Compound of formula (XIX), DIPEA, NMP;
h) Compound of formula (XIV), Pd(di-t-bpf)Cl$_2$, NaHCO$_3$, dioxane (aq);
i) HCl/dioxane, toluene;
j) (i) NaOH(aq), EtOAc;
   (ii) n-BuOAc, TBME.

Scheme 7: Synthesis of 5,7-dichloro-1,6-naphthyridine

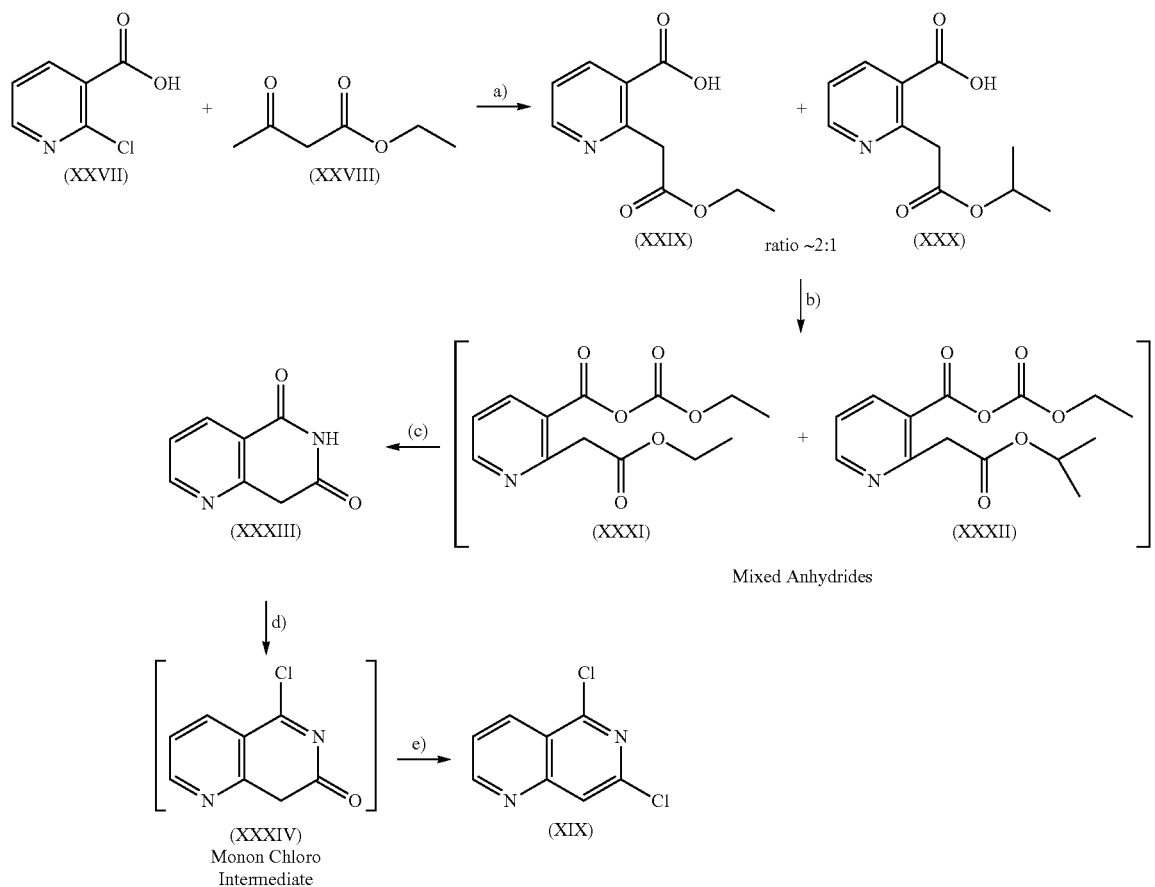

a) Cu(OAc)$_2$, tert-BuOK, IPA;
b) TEA, THF, ClCO$_2$Et;
c) NH$_3$(aq), HCl(aq);
d) POCl$_3$, Me$_4$NCl, reflux.

Scheme 8: Synthesis of 1-(1,1-dimethylethyl)-4-(4,4,5,5-tetramethyl-1,3,2-dioxaborolan-2-yl)-1H-pyrazole

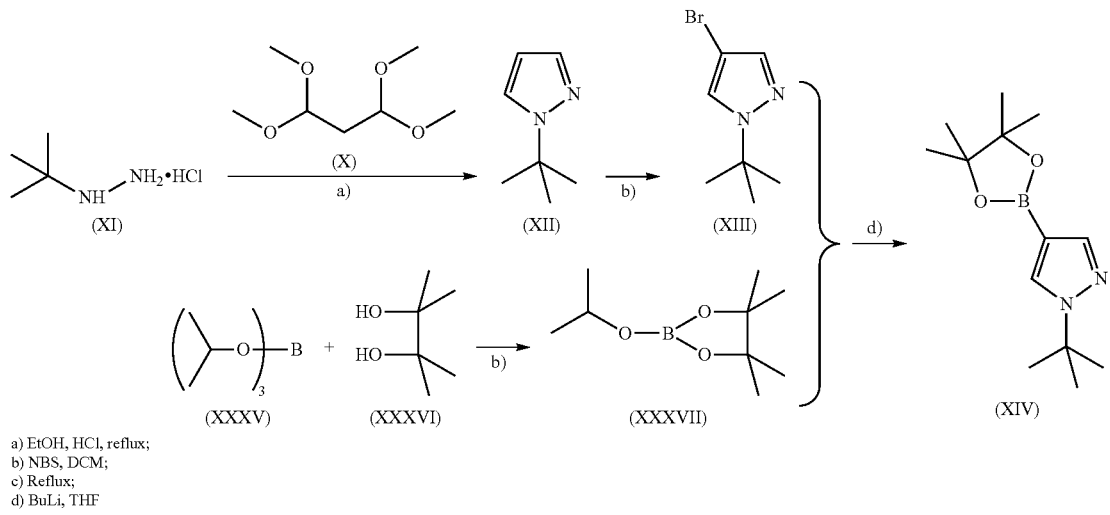

a) EtOH, HCl, reflux;
b) NBS, DCM;
c) Reflux;
d) BuLi, THF

Compounds of formulae (IV), (X), (XI), (XV), (XVII), (XXVII), (XXVIII), (XXXV) and (XXXVI) are commercially available from, for example, Sigma-Aldrich UK.

Thus, in one embodiment, the present invention provides a process for preparing a compound of formula (I) which process comprises reacting a 1,6-naphthyridine compound of formula (III):

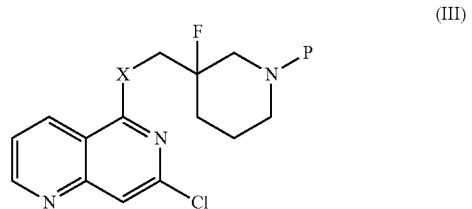

wherein P is a protecting group and X is as hereinbefore defined;
with a pyrazole boronic ester/acid compound of formula (XXVI):

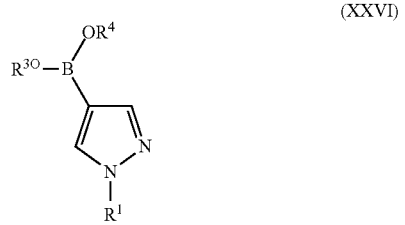

wherein $R^3$ and $R^4$ which may be the same or different, are each hydrogen, $C_{1-6}$ alkyl or $R^3$ and $R^4$ may be joined to form a $C_{1-3}$alkylene group optionally substituted by up to four methyl groups, for instance —C(Me)$_2$C(Me)$_2$-; and
$R^1$ is as hereinbefore defined;
in the presence of a catalyst, under conditions typically used for a boronic ester/acid coupling; and
thereafter, removing the protecting group P.

Examples of protecting groups and the means for their removal can be found in T. W. Greene 'Protective Groups in Organic Synthesis' (J. Wiley and Sons, 1991). Suitable amine protecting groups include, but are not restricted to, sulphonyl (such as tosyl), acyl (such as benzyloxycarbonyl or t-butoxycarbonyl) and arylalkyl (such as benzyl), which may be removed by hydrolysis or hydrogenolysis as appropriate. Other suitable amine protecting groups include trifluoroacetyl (—C(O)CF$_3$), which may be removed by base catalysed hydrolysis, or a solid phase resin bound benzyl group, such as a Merrifield resin bound 2,6-dimethoxybenzyl group (Ellman linker) which may be removed by acid catalysed hydrolysis (using, for example, trifluoroacetic acid).

In one embodiment of the present invention the protecting group (P) is selected from tert-butyloxycarbonyl "BOC" and 9-fluorenylmethyloxycarbonyl "FMOC".

It will be noted that, for synthetic efficiency, a precursor which is substantially enantiomerically pure is obtained as early as possible in the overall synthesis, in this instance, in the first stage of Scheme I. Thus, enantioselective fluorinaton of the piperidine nucleus at the 3-position, using an optically active catalyst ([(S)-(−)-2,2'-bisphosphino)-1,1'-binaphthyl] palladium (II) dihydrate ditriflate), leads to an enantiomerically enriched fluoro-product. This is then further resolved to give substantially enantiomerically pure product using, for instance, preparative chiral HPLC.

A compound of formula (I) may be prepared by the general synthetic schemes described hereinabove, using the racemic version of the catalyst ([(−)-2,2'-bisphosphino)-1,1'-binaphthyl]palladium (II) dihydrate ditriflate), in the first stage of Scheme 1, so there is no enantiomeric enrichment, and racemic intermediates are then used throughout. A compound of formula (II) may then be prepared from the corresponding, racemic compound of formula (I), or an amine protected precursor, by methods known in the art for chiral resolution, in particular (preparative) chiral HPLC. Alternatively, resolution may carried out at an earlier stage, if so desired, for instance, in Scheme 4, after stage c), after coupling of racemic amine to the 1,6-naphthyridine core.

Compounds of the present invention are useful as inhibitors of Syk and thus potentially of use in treating some cancer therapies, in particular heme malignancies, as well as inflammatory conditions which involve B cells, and also diseases resulting from inappropriate mast and basophil cell activation, for instance allergic and inflammatory diseases such as cutaneous mast cell mediated diseases including acute and chronic urticaria, mastocytosis, atopic dermatitis and autoimmune diseases such as cutaneous lupus and autoimmune bullous conditions including pemphigus and pemphigoid.

They may also be of use in treatment of acute conditions involving the mast cell such as post operative ileus.

Thus, in one embodiment, the present invention provides a compound of formula (I), or a pharmaceutically acceptable salt thereof, for use in therapy.

In one embodiment, the present invention provides a compound of formula (I) or a pharmaceutically acceptable salt thereof, for use in inhibiting spleen tyrosine kinase (Syk).

In another embodiment, the present invention provides a method of inhibiting spleen tyrosine kinase (Syk), which comprises administering to a subject in need thereof a therapeutically effective amount of a compound of formula (I) or a pharmaceutically acceptable salt thereof.

Syk inhibitors may be useful in cancer therapy, specifically heme malignancies, particularly Non-Hodgkin's Lymphomas including follicular (FL), mantle cell, small lymphocytic lymphoma/chronic lymphocytic lymphoma (SLL/CLL), Burkitt and diffuse large B cell (DLBCL) lymphomas.

Accordingly, in one embodiment, the present invention provides a compound of formula (I) or a pharmaceutically acceptable salt thereof, for use in the treatment of cancer, for example heme malignancies, particularly Non-Hodgkin's lymphomas including follicular (FL), mantle cell, small lymphocytic lymphoma/chronic lymphocytic lymphoma (SLL/CLL), Burkitt and diffuse large B cell (DLBCL) lymphomas.

In another embodiment, the present invention provides a method of treating cancer, specifically heme malignancies, particularly Non-Hodgkin's Lymphomas including follicular (FL), mantle cell, small lymphocytic lymphoma/chronic lymphocytic lymphoma (SLL/CLL), Burkitt and diffuse large B cell (DLBCL) lymphomas, which method comprises administering to a patient in need thereof an effective amount of a compound of formula (I), or a pharmaceutically acceptable salt thereof.

In a further embodiment, the present invention provides the use of a compound of formula (I) or a pharmaceutically acceptable salt thereof, for the manufacture of a medicament for the treatment of cancer, for example heme malignancies, particularly Non-Hodgkin's lymphomas including follicular (FL), mantle cell, small lymphocytic lymphoma/chronic lymphocytic lymphoma (SLL/CLL), Burkitt and diffuse large B cell (DLBCL) lymphomas.

Compounds of the present invention may also be used in cancer chemotherapy in combination with other classes of cancer chemotherapy agents which are known in the art. Representative classes of agents for use in such combinations for Non-Hodgkin's Lymphomas include rituximab, BEXXAR (tositumomab and Iodine I 131 tositumomab), pixantrone and chemotherapy. Combination of compounds of the present invention may also be used in combination with the CHOP drug regime (cyclophosphamide, adriamycin, vincristine, prednisone) or CHOP plus rituximab (CHOP+R).

Compounds of the present invention are potentially of use in treating autoimmune conditions which involve B cells and/or macrophage activation, for instance Systemic Lupus Erythematosus (SLE), Sjorgens Syndrome, Wegners granulomatosis and other vasculitides, bullous pemphigoid and pemphigus, idiopathic thrombocytopenic purpura (ITP), giant cell arteriosis, glomerulonephritis, chronic transplant rejection, and rheumatoid arthritis.

In one embodiment, the present invention provides a compound of formula (I) or a pharmaceutically acceptable salt thereof, for use in the treatment of an autoimmune condition, for example systemic lupus erythematosus (SLE), discoid (cutaneous) lupus, Sjorgens syndrome, Wegners granulomatosis and other vasculitides, bullous pemphigoid and pemphigus, idiopathic thrombocytopenic purpura (ITP), giant cell arteriosis, glomerulonephritis, chronic transplant rejection, and rheumatoid arthritis. In another embodiment, the present invention provides a compound of formula (I) or a pharmaceutically acceptable salt thereof for use in the treatment of rheumatoid arthritis. In a further embodiment, the present invention provides a compound which is 7-[1-(1,1-dimethylethyl)-1H-pyrazol-4-yl]-N-{[(3S)-3-fluoro-3-piperidinyl] methyl}-1,6-naphthyridin-5-amine or a pharmaceutically acceptable salt thereof for use in the treatment of rheumatoid arthritis.

In one embodiment, the present invention provides a method of treating an autoimmune condition, for example systemic lupus erythematosus (SLE), discoid (cutaneous) lupus, Sjorgens syndrome, Wegners granulomatosis and other vasculitides, bullous pemphigoid and pemphigus, idiopathic thrombocytopenic purpura (ITP), giant cell arteriosis, glomerulonephritis, chronic transplant rejection and rheumatoid arthritis, which method comprises administering to a patient in need thereof a therapeutically effective amount of a compound of formula (I) or a pharmaceutically acceptable salt thereof. In another embodiment, the present invention provides a method of treating rheumatoid arthritis, which method comprises administering to a patient in need thereof a therapeutically effective amount of a compound of formula (I) or a pharmaceutically acceptable salt thereof. In a further embodiment, the present invention provides a method of treating rheumatoid arthritis, which method comprises administering to a patient in need thereof a therapeutically effective amount of a compound which is 7-[1-(1,1-dimethylethyl)-1H-pyrazol-4-yl]-N-{[(3S)-3-fluoro-3-piperidinyl] methyl}-1,6-naphthyridin-5-amine or a pharmaceutically acceptable salt thereof.

In one embodiment, the present invention provides the use of a compound of formula (I) or a pharmaceutically acceptable salt thereof, for the manufacture of a medicament for the treatment of an autoimmune condition, for example systemic lupus erythematosus (SLE), discoid (cutaneous) lupus, Sjorgens syndrome, Wegners granulomatosis and other vasculitides, bullous pemphigoid and pemphigus, idiopathic thrombocytopenic purpura (ITP), giant cell arteriosis, glomerulonephritis, chronic transplant rejection and rheumatoid arthritis. In another embodiment, the present invention provides the use of a compound of formula (I) or a pharmaceutically acceptable salt thereof for the manufacture of a medicament for the treatment of rheumatoid arthritis. In a further embodiment, the present invention provides the use of a compound which is 7-[1-(1,1-dimethylethyl)-1H-pyrazol-4-yl]-N-{[(3S)-3-fluoro-3-piperidinyl]methyl}-1,6-naphthyridin-5-amine or a pharmaceutically acceptable salt thereof for the manufacture of a medicament for the treatment of rheumatoid arthritis.

Compounds of the present invention are potentially of use in treating chronic idiopathic urticaria with and without autoantibody status (now known as chronic spontaneous urticaria).

In one embodiment, the present invention provides a compound of formula (I) or a pharmaceutically acceptable salt thereof for use in the treatment of chronic spontaneous urticaria. In another embodiment, the present invention provides a compound which is 7-[1-(1,1-dimethylethyl)-1H-pyrazol- 4-yl]-N-{[(3S)-3-fluoro-3-piperidinyl]methyl}-1,6-naphthyridin-5-amine or a pharmaceutically acceptable salt thereof for use in the treatment chronic spontaneous urticaria.

In one embodiment, the present invention provides a method of treating chronic spontaneous urticaria, which method comprises administering to a patient in need thereof a therapeutically effective amount of a compound of formula (I) or a pharmaceutically acceptable salt thereof. In another embodiment, the present invention provides a method of treating chronic spontaneous urticaria, which method comprises administering to a patient in need thereof a therapeutically effective amount of a compound of which is 7-[1-(1,1-dimethylethyl)-1H-pyrazol-4-yl]-N-{[(3S)-3-fluoro-3-piperidinyl]methyl}-1,6-naphthyridin-5-amine or a pharmaceutically acceptable salt thereof.

In one embodiment, the present invention provides the use of a compound of formula (I) or a pharmaceutically acceptable salt thereof for the manufacture of a medicament for the treatment of chronic spontaneous urticaria. In another embodiment, the present invention provides the use of a compound which is 7-[1-(1,1-dimethylethyl)-1H-pyrazol-4-yl]-N-{[(3S)-3-fluoro-3-piperidinyl]methyl}-1,6-naphthyridin-5-amine or a pharmaceutically acceptable salt thereof for the manufacture of a medicament for the treatment of chronic spontaneous urticaria.

In one embodiment, the present invention provides a compound of formula (I) or a pharmaceutically acceptable salt thereof, for use in the treatment of an inflammatory disease which involves B cells.

In one embodiment, the present invention provides a method of treating an inflammatory disease which involves B cells which method comprises administering to a patient in need thereof an effective amount of a compound of formula (I), or a pharmaceutically acceptable salt thereof.

In one embodiment, the present invention provides the use of a compound of formula (I) or a pharmaceutically acceptable salt thereof, for the manufacture of a medicament for the treatment of an inflammatory disease which involves B cells.

Compounds of the present invention are potentially of use in treating diseases resulting from inappropriate mast cell activation, for instance allergic and inflammatory diseases.

In one embodiment, the present invention provides a compound of formula (I) or a pharmaceutically acceptable salt thereof, for use in the treatment of a disease associated with inappropriate mast and/or basophil cell activation, including those diseases with skin manifestations.

In one embodiment, the present invention provides a method of treating a disease associated with inappropriate mast and/or basophil cell activation which comprises administering to a patient in need thereof an effective amount of a compound of formula (I), or a pharmaceutically acceptable salt thereof. In another embodiment, the present invention provides a method of treating a disease associated with inappropriate mast and/or basophil cell activation including those diseases with skin manifestations, which comprises administering to a patient in need thereof an effective amount of a compound of formula (I), or a pharmaceutically acceptable salt thereof.

In one embodiment, the present invention provides the use of a compound of formula (I) or a pharmaceutically acceptable salt thereof, for the manufacture of a medicament for the treatment of a disease associated with inappropriate mast and/or basophil cell activation.

In one embodiment, the present invention provides a compound of formula (I) or a pharmaceutically acceptable salt thereof, for use in the treatment of an inflammatory disease and/or allergic disorder for example, chronic obstructive pulmonary disease (COPD), adult respiratory distress syndrome (ARDS), asthma, severe asthma, ulcerative colitis, Crohn's disease, bronchitis, conjunctivitis, psoriasis, scleroderma, dermatitis, allergy, rhinitis, cutaneous lupus, autoimmune bullous conditions including pemphigus and pemphigoid, mastocytosis and anaphylaxis.

In one embodiment, the present invention provides a method of treating an inflammatory disease and/or allergic disorder for example, chronic obstructive pulmonary disease (COPD), adult respiratory distress syndrome (ARDS), asthma, severe asthma, ulcerative colitis, Crohn's disease, bronchitis, conjunctivitis, psoriasis, scleroderma, dermatitis, allergy, rhinitis, cutaneous lupus, autoimmune bullous conditions including pemphigus and pemphigoid, mastocytosis and anaphylaxis, which method comprises administering to a patient in need thereof a therapeutically effective amount of a compound of formula (I) or a pharmaceutically acceptable salt thereof.

In one embodiment, the present invention provides the use of a compound of formula (I) or a pharmaceutically acceptable salt thereof, for the manufacture of a medicament for the treatment of an inflammatory disease and/or allergic disorder for example, chronic obstructive pulmonary disease (COPD), adult respiratory distress syndrome (ARDS), asthma, severe asthma, ulcerative colitis, Crohn's disease, bronchitis, conjunctivitis, psoriasis, scleroderma, dermatitis, allergy, rhinitis, cutaneous lupus, autoimmune bullous conditions including pemphigus and pemphigoid, mastocytosis and anaphylaxis.

In one embodiment, the present invention provides a compound of formula (I) or a pharmaceutically acceptable salt thereof, for use in the treatment of an inflammatory disease which involves inappropriate mast cell activation.

In one embodiment, the present invention provides a method of treating an inflammatory disease which involves inappropriate mast cell activation which method comprises administering to a patient in need thereof an effective amount of a compound of formula (I) or a pharmaceutically acceptable salt thereof. In another embodiment, the present invention provides a method of treating an inflammatory disease which involves inappropriate mast cell activation which method comprises administering to a patient in need thereof an effective amount of a compound of formula (I) or a pharmaceutically acceptable salt thereof.

In one embodiment, the present invention provides the use of a compound of formula (I) or a pharmaceutically acceptable salt thereof, for the manufacture of a medicament for the treatment of an inflammatory disease which involves inappropriate mast cell activation.

In one embodiment, the present invention provides a compound of formula (I) or a pharmaceutically acceptable salt thereof, for use in the treatment of an allergic disorder which involves inappropriate mast cell activation.

In one embodiment, the present invention provides a method of treating an allergic disorder which involves inappropriate mast cell activation which method comprises administering to a patient in need thereof an effective amount of a compound of formula (I) or a pharmaceutically acceptable salt thereof. In another embodiment, the present invention provides a method of treating an allergic disorder which involves inappropriate mast cell activation which method comprises administering to a patient in need thereof an effective amount of a compound of formula (I) or a pharmaceutically acceptable salt thereof.

In one embodiment, the present invention provides the use of a compound of formula (I) or a pharmaceutically acceptable salt thereof, for the manufacture of a medicament for the treatment of an allergic disorder which involves inappropriate mast cell activation.

Diseases and pathological conditions thought to be mediated by Syk include inflammatory and allergic disorders involving mast cell activation, such as chronic obstructive pulmonary disease (COPD), adult respiratory distress syndrome (ARDS), severe asthma, ulcerative colitis, Crohn's disease, bronchitis, conjunctivitis, psoriasis, scleroderma, chronic and acute urticaria, including chronic spontaneous urticaria and contact and physical urticarias, dermatitis, allergy, rhinitis, mastocytosis and anaphylaxis.

Compounds of the present invention may also be used in combination with other classes of therapeutic agents, for example selected from anti-inflammatory agents, anticholinergic agents (particularly an $M_1/M_2/M_3$ receptor antagonist), $\beta_2$-adrenoreceptor agonists, antiinfective agents such as antibiotics or antivirals, or antihistamines.

In another embodiment, compounds of the present invention may also be used in combination with other classes of therapeutic agents which are known in the art for treating autoimmune diseases, for instance disease modifying anti-rheumatic drugs including cyclosporine, methotrexate, sulphasalazine, prednisone, leflunomide, and chloroquine/hydrochloroquine and also biopharmaceutical agents such as humanised monoclonal antibodies (mabs), for example including anti-TNF alpha blockers such as remicade, enbrel and humira and B cell depleting therapies such as rituximab and ofatumumab, and anti-Blys mabs such as belilumab.

The invention thus provides, a combination comprising a compound of formula (I) or a pharmaceutically acceptable salt thereof together with one or more other therapeutically active agents, for example selected from an anti-inflammatory agent such as a corticosteroid or an NSAID, an anticholinergic agent, a $\beta_2$-adrenoreceptor agonist, an antiinfective agent such as an antibiotic or an antiviral, an antihistamine, a disease modifying anti-rheumatic drug, and a biopharmaceutical agent such as humanised monoclonal antibodies (mabs), B cell depleting therapies and anti-Blys mabs. One embodiment of the invention encompasses combinations comprising a compound of formula (I) or a pharmaceutically acceptable salt thereof together with a $\beta_2$-adrenoreceptor agonist, and/or an anticholinergic, and/or a PDE-4 inhibitor, and/or an antihistamine, and/or a disease modifying anti-rheumatic drug, and/or a biopharmaceutical agent.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimise the activity and/or stability and/or physical characteristics, such as solubility, of the therapeutic ingredient. It will be clear also that, where appropriate, the therapeutic ingredients may be used in optically pure form.

Examples of $\beta_2$-adrenoreceptor agonists include salmeterol (which may be a racemate or a single enantiomer such as the R-enantiomer), salbutamol (which may be a racemate or a single enantiomer such as the R-enantiomer), formoterol (which may be a racemate or a single stereoisomer such as the R,R-stereoisomer), salmefamol, fenoterol, carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt or free base of salbutamol or the fumarate salt of formoterol. In one embodiment the $\beta_2$-adrenoreceptor agonists are long-acting $\beta_2$-adrenoreceptor agonists, for example, compounds which provide effective bronchodilation for about 12 hours or longer.

Other $\beta_2$-adrenoreceptor agonists include those described in WO02/066422, WO02/070490, WO02/076933, WO03/024439, WO03/072539, WO03/091204, WO04/016578, WO04/022547, WO04/037807, WO04/037773, WO04/037768, WO04/039762, WO04/039766, WO01/42193 and WO03/042160.

Examples of $\beta_2$-adrenoreceptor agonists include:
3-(4-{[6-({(2R)-2-hydroxy-2-[4-hydroxy-3-(hydroxymethyl)phenyl]ethyl}amino)hexyl]oxy}butyl)benzenesulfonamide;
3-(3-{[7-({(2R)-2-hydroxy-2-[4-hydroxy-3-hydroxymethyl)phenyl]ethyl}-amino)heptyl]oxy}propyl)benzenesulfonamide;
4-{(1R)-2-[(6-{2-[(2,6-dichlorobenzyl)oxy]ethoxy}hexyl) amino]-1-hydroxyethyl}-2-(hydroxymethyl)phenol;
4-{(1R)-2-[(6-{4-[3-(cyclopentylsulfonyl)phenyl] butoxy}hexyl)amino]-1-hydroxyethyl}-2-(hydroxymethyl)phenol;
N-[2-hydroxyl-5-[(1R)-1-hydroxy-2-[[2-4-[[(2R)-2-hydroxy-2-phenylethyl]amino]phenyl]ethyl]amino]ethyl] phenyl]formamide;
N-2{2-[4-(3-phenyl-4-methoxyphenyl)aminophenyl]ethyl}-2-hydroxy-2-(8-hydroxy-2(1H)-quinolinon-5-yl)ethylamine; and
5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

The $\beta_2$-adrenoreceptor agonist may be in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, sulphanilic, naphthaleneacrylic, benzoic, 4-methoxybenzoic, 2- or 4-hydroxybenzoic, 4-chlorobenzoic and 4-phenylbenzoic acid.

Examples of corticosteroids may include those described in WO02/088167, WO02/100879, WO02/12265, WO02/12266, WO05/005451, WO05/005452, WO06/072599 and WO06/072600.

Anti-inflammatory corticosteroids are well known in the art. Representative examples include fluticasone propionate (e.g. see U.S. Pat. No. 4,335,121), fluticasone furoate (e.g. see U.S. Pat. No. 7,101,866), beclomethasone 17-propionate ester, beclomethasone 17,21-dipropionate ester, dexamethasone or an ester thereof, mometasone or an ester thereof (e.g. mometasone furoate), ciclesonide, budesonide, flunisolide, methyl prednisolone, prednisolone, dexamethasone and 6α,9α-difluoro-11β-hydroxy-16α-methyl-3-oxo-17α-(2,2, 3,3-tetramethycyclopropylcarbonyl)oxy-androsta-1,4-diene-17β-carbothioic acid S-cyanomethyl ester. Further examples of anti-inflammatory corticosteroids are described in WO02/088167, WO02/100879, WO02/12265, WO02/12266, WO05/005451, WO05/005452, WO06/072599 and WO06/072600.

Non-steroidal compounds having glucocorticoid agonism that may possess selectivity for transrepression over transactivation and that may be useful in combination therapy include those covered in the following published patent applications and patents: WO03/082827, WO98/54159, WO04/005229, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651, WO03/08277, WO06/000401, WO06/000398, WO06/015870, WO06/108699, WO07/000,334 and WO07/054,294.

Examples of anti-inflammatory agents include non-steroidal anti-inflammatory drugs (NSAID's).

Examples of NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example montelukast), iNOS inhibitors, tryptase and elastase inhibitors, beta-2 integrin antagonists and adenosine receptor agonists or antagonists (e.g. adenosine 2a agonists), cytokine antagonists (for example chemokine antagonists, such as a CCR3 antagonist) or inhibitors of cytokine synthesis, or 5-lipoxygenase inhibitors. An iNOS (inducible nitric oxide synthase inhibitor) is preferably for oral administration. Examples of iNOS inhibitors include those disclosed in WO93/13055, WO98/30537, WO02/50021, WO95/34534 and WO 99/62875. Examples of CCR3 inhibitors include those disclosed in WO02/26722.

Examples of PDE4 inhibitors include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms (e.g. see U.S. Pat. No. 5,552,438).

Other compounds include AWD-12-281 from Elbion (Hofgen, N. et al. 15th EFMC Int Symp Med Chem (September 6-10, Edinburgh) 1998, Abst P.98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (e.g. see WO99/47505) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds are disclosed in the published international patent application WO04/024728 (Glaxo Group Ltd), WO04/056823 (Glaxo Group Ltd) and WO04/103998 (Glaxo Group Ltd).

Examples of anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$ receptors or pan-antagonists of the $M_1/M_2/M_3$ receptors. Exemplary compounds for administration via inhalation include ipratropium (for example, as the bromide, CAS 22254-24-6, sold under the name Atrovent), oxitropium (for example, as the bromide, CAS 30286-75-0) and tiotropium (for example, as the bromide, CAS136310-93-5, sold under the name Spiriva). Also of interest are revatropate (for example, as the hydrobromide, CAS 262586-79-8) and LAS-34273 which is disclosed in WO01/04118. Exemplary compounds for oral administration include pirenzepine (CAS 28797-61-7), darifenacin (CAS 133099-04-4, or CAS 133099-07-7 for the hydrobromide sold under the name Enablex), oxybutynin (CAS 5633-20-5, sold under the name Ditropan), terodiline (CAS 15793-40-5), tolterodine (CAS 124937-51-5, or CAS 124937-52-6 for the tartrate, sold under the name Detrol), otilonium (for example, as the bromide, CAS 26095-59-0, sold under the name Spasmomen), trospium chloride (CAS 10405-02-4) and solifenacin (CAS 242478-37-1, or CAS 242478-38-2 for the succinate also known as YM-905 and sold under the name Vesicare).

Other anticholinergic agents include compounds which are disclosed in U.S. patent application 60/487,981 including, for example:
(3-endo)-3-(2,2-di-2-thienylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane 4-methylbenzenesulfonate;
(3-endo)-8,8-dimethyl-3-[2-phenyl-2-(2-thienyl)ethenyl]-8-azoniabicyclo[3.2.1]octane bromide; and
(3-endo)-8,8-dimethyl-3-[2-phenyl-2-(2-pyridinyl)ethenyl]-8-azoniabicyclo[3.2.1]octane bromide.

Further anticholinergic agents include compounds which are disclosed in U.S. patent application 60/511,009 including, for example:
(endo)-3-(2-methoxy-2,2-di-thiophen-2-yl-ethyl)-8,8-dimethyl-8-azoniabicyclo[3.2.1]octane iodide;
3-((endo)-8-methyl-8-aza-bicyclo[3.2.1]oct-3-yl)-2,2-diphenyl-propionitrile;
(endo)-8-methyl-3-(2,2,2-triphenyl-ethyl)-8-aza-bicyclo[3.2.1]octane;
3-((endo)-8-methyl-8-aza-bicyclo[3.2.1]oct-3-yl)-2,2-diphenyl-propionamide;
3-((endo)-8-methyl-8-aza-bicyclo[3.2.1]oct-3-yl)-2,2-diphenyl-propionic acid;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
3-((endo)-8-methyl-8-aza-bicyclo[3.2.1]oct-3-yl)-2,2-diphenyl-propan-1-ol;
N-benzyl-3-((endo)-8-methyl-8-aza-bicyclo[3.2.1]oct-3-yl)-2,2-diphenyl-propionamide;
(endo)-3-(2-carbamoyl-2,2-diphenyl-ethyl)-8,8-dimethyl-8-azonia-bicyclo[3.2.1]octane iodide;
1-benzyl-3-[3-((endo)-8-methyl-8-aza-bicyclo[3.2.1]oct-3-yl)-2,2-diphenyl-propyl]-urea;
1-ethyl-3-[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-acetamide;
N-[3-((endo)-8-methyl-8-aza-bicyclo[3.2.1]oct-3-yl)-2,2-diphenyl-propyl]-benzamide;
3-((endo)-8-methyl-8-aza-bicyclo[3.2.1]oct-3-yl)-2,2-di-thiophen-2-yl-propionitrile;
(endo)-3-(2-cyano-2,2-di-thiophen-2-yl-ethyl)-8,8-dimethyl-8-azonia-bicyclo[3.2.1]octane iodide;
N-[3-((endo)-8-methyl-8-aza-bicyclo[3.2.1]oct-3-yl)-2,2-diphenyl-propyl]-benzenesulfonamide;
[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-methanesulfonamide; and
(endo)-3-{2,2-diphenyl-3-[(1-phenyl-methanoyl)-amino]-propyl}-8,8-dimethyl-8-azonia-bicyclo[3.2.1]octane bromide.

Further compounds include:
(endo)-3-(2-methoxy-2,2-di-thiophen-2-yl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
(endo)-3-(2-carbamoyl-2,2-diphenyl-ethyl)-8,8-dimethyl-8-azonia-bicyclo[3.2.1]octane iodide;
(endo)-3-(2-cyano-2,2-di-thiophen-2-yl-ethyl)-8,8-dimethyl-8-azonia-bicyclo[3.2.1]octane iodide; and
(endo)-3-{2,2-diphenyl-3-[(1-phenyl-methanoyl)-amino]-propyl}-8,8-dimethyl-8-azonia-bicyclo[3.2.1]octane bromide.

In one embodiment the invention provides a combination comprising a compound of formula (I), or a pharmaceutically acceptable salt thereof, together with an H1 antagonist. Examples of H1 antagonists include, without limitation, methapyrilene, desloratadine, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine. In a further embodiment the invention provides a combination comprising a compound of formula (I), or a pharmaceutically acceptable salt thereof, together with an H3 antagonist (and/or inverse agonist). Examples of H3 antagonists include, for example, those compounds disclosed in WO2004/035556 and in WO2006/045416. Other histamine receptor antagonists which may be used in combination with the compounds of formula (I), or a pharmaceutically acceptable salt thereof, include antagonists (and/or inverse agonists) of the H4 receptor, for example, the compounds disclosed in Jablonowski et al., *J. Med. Chem.* 46:3957-3960 (2003).

In one embodiment there is provided, a combination comprising a compound of formula (I) or a pharmaceutically acceptable salt thereof together with a corticosteroid. In another embodiment there is provided, a combination comprising a compound of formula (I) or a pharmaceutically acceptable salt thereof together with an NSAID. In another embodiment there is provided, a combination comprising a compound of formula (I) or a pharmaceutically acceptable salt thereof together with an anticholinergic. In another embodiment there is provided, a combination comprising a compound of formula (I) or a pharmaceutically acceptable salt thereof together with a $\beta_2$-adrenoreceptor agonist. In another embodiment there is provided, a combination comprising a compound of formula (I) or a pharmaceutically acceptable salt thereof together with an antiinfective. In another embodiment there is provided, a combination comprising a compound of formula (I) or a pharmaceutically acceptable salt thereof together with an antihistamine. In another embodiment there is provided, a combination comprising a compound of formula (I) or a pharmaceutically acceptable salt thereof together with a disease modifying anti-rheumatic drug. In a further embodiment there is provided, a combination comprising a compound of formula (I) or a pharmaceutically acceptable salt thereof together with a biopharmaceutical agent.

A compound of the present invention will normally, but not necessarily, be formulated into pharmaceutical compositions prior to administration to a patient. Accordingly, in one embodiment the invention is directed to pharmaceutical compositions comprising a compound of formula (I), or a pharmaceutically acceptable salt thereof, and one or more pharmaceutically acceptable excipients. In another embodiment the invention is directed to a pharmaceutical composition comprising 7-[1-(1,1-dimethylethyl)-1H-pyrazol-4-yl]-N-{[(3S)-3-fluoro-3-piperidinyl]methyl}-1,6-naphthyridin-5-amine or a pharmaceutically acceptable salt thereof and one or more pharmaceutically acceptable excipients.

The pharmaceutical compositions of the invention may be prepared and packaged in bulk form wherein a safe and effective amount of a compound of the invention can be extracted and then given to the patient, such as with powders or syrups. Alternatively, the pharmaceutical compositions of the invention may be prepared and packaged in unit dosage form wherein each physically discrete unit contains a safe and effective amount of a compound of the invention. The pharmaceutical compositions of the invention may also be prepared and packaged in a sub-unit dosage form wherein two or more sub-unit dosage forms provide the unit dosage form. When prepared in unit dosage form, the pharmaceutical compositions of the invention typically contain from about 0.1 to 99.9 wt. %, of a compound of the invention, depending on the nature of the formulation.

In addition, the pharmaceutical compositions of the invention may optionally further comprise one or more additional pharmaceutically active compounds.

As used herein, "pharmaceutically acceptable excipient" means a pharmaceutically acceptable material, composition or vehicle involved in giving form or consistency to the pharmaceutical composition. Each excipient must be compatible with the other ingredients of the pharmaceutical composition when commingled, such that interactions which would substantially reduce the efficacy of the compound of the invention when administered to a patient and would result in pharmaceutically unacceptable compositions are avoided. In addition, each excipient must of course be of sufficiently high purity to render it pharmaceutically acceptable.

Compositions of the present invention comprising a compound of formula (I), or a pharmaceutically acceptable salt thereof and the pharmaceutically acceptable excipient or excipients will typically be provided as a dosage form adapted for administration to the patient by the desired route of administration. For example, dosage forms include those adapted for: (1) oral administration, such as tablets, capsules, caplets, pills, troches, powders, syrups, elixers, suspensions, solutions, emulsions, sachets, and cachets; (2) topical dermal administration, such as creams, ointments, lotions, solutions, pastes, sprays, foams, and gels, (3) inhalation, such as aerosols and solutions; (4) intranasal administration, such as solutions or sprays; and (5) parenteral administration, such as sterile solutions, suspensions, and powders for reconstitution and.

It will be appreciated that dosage forms adapted for oral administration are commonly used for treating autoimmune disease including rheumatoid arthritis and systemic lupus erythematosus; cancer including heme malignancies; and chronic spontaneous urticaria. Dosage forms adapted for topical administration to the skin are commonly used for treating atopic dermatitis, psoriasis and chronic and acute urticaria conditions, and autoimmune bullous conditions including pemphigus and pemphigoid. Dosage forms adapted for inhalation or oral administration are commonly used for treating COPD and asthma; whilst dosage forms adapted for intranasal administration are commonly used for treating allergic rhinitis.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound of the present invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavouring agents, flavour masking agents, colouring agents, anticaking agents, humectants, chelating agents, plasticizers, viscosity increasing agents, antioxidants, preservatives, stabilizers, surfactants and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), Remington: The Science and Practice of Pharmacy, (Lippincott Williams & Wilkins), The Handbook of Pharmaceutical Additives (Gower Publishing Limited), and The Handbook of Pharmaceutical Excipients (the American Pharmaceutical Association and the Pharmaceutical Press).

The pharmaceutical compositions of the invention are prepared using techniques and methods known to those skilled in the art. Some of the methods commonly used in the art are described in Remington's Pharmaceutical Sciences (Mack Publishing Company).

Oral solid dosage forms such as tablets will typically comprise one or more pharmaceutically acceptable excipients, which may for example help impart satisfactory processing and compression characteristics, or provide additional desirable physical characteristics to the tablet. Such pharmaceutically acceptable excipients may be selected from diluents, binders, glidants, lubricants, disintegrants, colourants, flavourants, sweetening agents, polymers, waxes or other solubility-modulating materials.

Dosage forms for topical administration to the skin may, for example, be in the form of ointments, creams, lotions, eye ointments, eye drops, ear drops, impregnated dressings, and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

Dosage forms for parenteral administration will generally comprise fluids, particularly intravenous fluids, i.e., sterile solutions of simple chemicals such as sugars, amino acids or electrolytes, which can be easily carried by the circulatory system and assimilated. Such fluids are typically prepared with water for injection USP. Fluids used commonly for intravenous (IV) use are disclosed in Remington: The Science and Practice of Pharmacy, (Lippincott Williams & Wilkins). The pH of such IV fluids may vary, and will typically be from 3.5 to 8, as known in the art.

Dosage forms for nasal or inhaled administration may conveniently be formulated as aerosols, solutions, drops, gels or dry powders.

Dosage forms for topical administration to the nasal cavity (nasal administration) include pressurised aerosol formulations and aqueous formulations administered to the nose by pressurised pump. Formulations which are non-pressurised and adapted for nasal administration are of particular interest. Suitable formulations contain water as the diluent or carrier for this purpose. Aqueous formulations for administration to the nose may be provided with conventional excipients such as buffering agents, tonicity modifying agents and the like. Aqueous formulations may also be administered to the nose by nebulisation.

Dosage forms for nasal administration are provided in a metered dose device. The dosage form may be provided as a fluid formulation for delivery from a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. In one embodiment, the fluid dispenser is of the general type described and illustrated in WO2005/044354A1. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO2005/044354A1.

Aerosol compositions, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2- tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, it is preferred that the pharmaceutical composition is a dry powder inhalable composition. Such a composition can comprise a powder base such as lactose, glucose, trehalose, mannitol or starch, the compound of formula (I) or (II) or a pharmaceutically acceptable salt thereof (preferably in particle-size-reduced form, e.g. in micronised form), and optionally a performance modifier such as L-leucine or another amino acid, cellobiose octaacetate and/or metals salts of stearic acid such as magnesium or calcium stearate. Preferably, the dry powder inhalable composition comprises a dry powder blend of lactose and the compound of formula (I) or a pharmaceutically acceptable salt thereof. The lactose is preferably lactose hydrate e.g. lactose monohydrate and/or is preferably inhalation-grade and/or fine-grade lactose. Preferably, the particle size of the lactose is defined by 90% or more (by weight or by volume) of the lactose particles being less than 1000 microns (micrometers) (e.g. 10-1000 microns e.g. 30-1000 microns) in diameter, and/or 50% or more of the lactose particles being less than 500 microns (e.g. 10-500 microns) in diameter. More preferably, the particle size of the lactose is defined by 90% or more of the lactose particles being less than 300 microns (e.g. 10-300 microns e.g. 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. Most importantly, it is preferable that about 3 to about 30% (e.g. about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 JD Zwolle, Netherlands).

Optionally, in particular for dry powder inhalable compositions, a pharmaceutical composition for inhaled administration can be incorporated into a plurality of sealed dose containers (e.g. containing the dry powder composition) mounted longitudinally in a strip or ribbon inside a suitable inhalation device. The container is rupturable or peel-openable on demand and the dose of e.g. the dry powder composition can be administered by inhalation via the device such as the DISKUS® device, marketed by GlaxoSmithKline. The DISKUS® inhalation device is for example described in GB 2242134 A, and in such a device at least one container for the pharmaceutical composition in powder form (the container or containers preferably being a plurality of sealed dose containers mounted longitudinally in a strip or ribbon) is defined between two members peelably secured to one another; the device comprises: a means of defining an opening station for the said container or containers; a means for peeling the members apart at the opening station to open the container; and an outlet, communicating with the opened container, through which a user can inhale the pharmaceutical composition in powder form from the opened container.

A composition of the present invention, for intranasal administration, may also be adapted for dosing by insufflation, as a dry powder formulation.

For dosage forms for inhaled administration, where the compound or a pharmaceutically acceptable salt of formula (I) is present as a dry powder or in suspension, then it is preferred that it is in a particle-size-reduced form. Preferably the size-reduced form is obtained or obtainable by micronisation. The preferable particle size of the size-reduced (e.g. micronised) compound or pharmaceutically acceptable salt is defined by a D50 value of about 0.5 to about 10 microns (for example as measured using laser diffraction).

It will be appreciated that when the compounds of the present invention are administered in combination with other therapeutic agents normally administered by the inhaled, intravenous, oral, topical or intranasal route, that the resultant pharmaceutical composition may be administered by the same routes.

The compounds of the present invention may conveniently be administered in amounts of, for example, 1 µg to 2 g. The precise dose will of course depend on the age and condition of the patient and the particular route of administration chosen.

Biological Test Methods

Compounds of the invention may be tested for in vitro activity in accordance with the following assays:

1. Basic Syk Enzyme Activity

3 µl of SYK lysate diluted 16-fold in assay buffer (20 mM TRIS pH 7.4, 0.01% BSA, 0.1% Pluronic F-68) was added to wells containing 0.1 µl of various concentrations of compound or DMSO vehicle (1.7% final) in a Greiner low volume 384 well black plate. Following 15 min pre-incubation at room temperature, the reaction was initiated by the addition of 3 µl of substrate reagent containing Y7 Sox peptide, (Invitrogen Cat. # KNZ3071, 5 µM final), ATP (35 µM final) and MgCl$_2$ (10 mM final) in assay buffer. The reaction was incubated at room temperature before measuring fluorescence intensity ($\lambda_{ex}$ 360/$\lambda_{em}$ 485) on an Envision plate reader (Perkin Elmer Life Sciences, Waltham, Mass., USA) at 15 min and 55 min post-substrate addition.

The compounds of Examples 1, 2, 3, 4, 5, 7, 8, 9A, 9B, 10, 11A and 11B (as the free base) were tested essentially as described above and were each found to have an average IC$_{50}$ value in this assay of <1 µM. The hydrochloric acid salts of compounds of Examples 1, 2, 3, 4 and 6 were tested essentially as described above and were each found to have an average IC$_{50}$ value in this assay of <1 µM.

The compounds of Examples 1, 2, 3, 4, 5, 7, 8, 9A, 9B, 10, 11A and 11B (as the free base) were tested essentially as described above and were each found to have an average pIC$_{50}$ value in this assay of ≥7.0. For example, Examples 1, 2, 3 and 4 (as the free base) were found to have average values of 7.6 (n=7), 7.7 (n=10), 7.2 (n=11) and 8.1 (n=11) respectively. The hydrochloric acid salts of compounds of Examples 1, 2, 3, 4 and 6 were tested essentially as described above and were each found to have an average pIC$_{50}$ value in this assay of ≥6.5.

Those skilled in the art will recognize that in vitro binding assays and cell-based assays for functional activity are subject to variability. Accordingly, it is to be understood that the values for the IC$_{50}$s and pIC$_{50}$s recited above are exemplary only.

Preparation of SYK Lysate i. Preparation of Ramos Cell Lysates

Ramos B Cells (human B cells of Burkitt's lymphoma, clone 296.4C10, ATCC) were cultured in suspension in growth medium (RPMI-1640, Sigma; supplemented with 2 mM L-glutamine, Gibco; 10 mM Hepes, Sigma; 1 mM sodium pyruvate, Sigma; 10% v/v heat-inactivated FCS, Gibco). Cells were grown in Corning Cellstacks (6360 cm$^2$) in 1 liter volume and viability and cell density were monitored daily. Cells were maintained at <1.5×10e6/ml and >92% viability.

Large scale production runs were generated from Large Scale Intermediate Aliquots (LSIA's) of frozen Ramos cells as this was found to give greater reproducibility than production from a continuously growing culture of Ramos cells.

The large scale production run cells were generated in four steps:
1. Thaw LSIA into 1× Cellstack;
2. Expand culture into 4× Cellstack;
3. Expand from 4 to 12× Cellstacks;
4. Harvest all 12× Cellstacks.

Cellstacks were harvested in 2 L centrifuge bottles using a Sorvall Mistral centrifuge, 2000 rpm, 10 minutes, 4° C. (2 L×2×10$^6$ cells/ml=4×10$^9$ cells total)

(Notes for cell scale-up: If the cell density exceeded 1.8× 10e6/ml or viability dropped below 90% the Syk prep obtained post-stimulation was likely to be of lower activity.)

Also, repeated passage of the Ramos cells seemed to have a detrimental effect on Syk activity when cell growth is done at scale (this did not seem to be the case in small scale cultures)—it is recommended always to use LSIA's and modular scale-up for large scale preps.

ii. Stimulation of Ramos Cells with Anti-IgM Ab to Produce Syk & Preparation of Lysates Cells were stimulated at 20×10$^6$ cells/ml using 15 ug/ml (final concentration) anti-IgM antibody. Following harvest (as described above), a total of 4×10$^9$ cells were resuspended in 180 ml pre-warmed (37° C.) DPBS in a Corning 500 ml centrifuge bottle. 20 ml anti-IgM antibody at 150 ug/ml were added to each 500 ml centrifuge bottle (working stock made up in DPBS pre-warmed to 37° C.). Cells were incubated for exactly 5 min at 37° C. following the addition of anti IgM antibody. Following 5 min stimulation, 300 ml ice-cold DPBS were added to each bottle to stop the stimulation (temperature drops to ~12° C.) then cells were centrifuged at 2000 rpm (Sorvall Legend RT+ centrifuge—pre-chilled to 4° C.). Cells were washed by resuspension in ice-cold DPBS and centrifugation as above. The cell pellet was then lysed in ice-cold lysis buffer containing 1% triton-x-100 at a ratio of 150 ul/1×10$^7$ cells (i.e. 48 ml lysis buffer). Following the addition of lysis buffer, the cells were pipetted up & down & kept on ice for 15 min. The clarified lysate was then obtained by centrifugation (Sorvall Evolution RC (SLA-1500 rotor, ~20,000 g (~14,500 rpm), 45 min, 4° C.).

Lysate was aliquoted, snap-frozen on dry-ice & stored at −80° C. prior to assay.

Materials

Ramos Cells: Human B cells of Burkitts lymphoma, clone 296.4C10 (ATCC).

Growth Media: 500 ml RPMI, 10% heat inactivated FCS, 2 mM L-Glutamine, 2 mM
  HEPES, 1 mM sodium pyruvate.
  RPMI: Sigma R0883, stores CT5652
  Foetal Calf Serum: Gibco 10099-141, stores CT2509
  L-Glutamine: 200 mM, Gibco 25030, stores CT3005
  HEPES: 1M, Sigma H0887, stores CT5637
  Sodium Pyruvate: 100 mM, Sigma S8636, stores CT7741
  Anti-IgM Ab: Goat anti-human IgM ((Fab')$_2$ fragments) in PBS. Invitrogen, custom-made preparation (azide free and low endotoxin levels). Catalogue no. NON0687, Lot 1411913. 2.74 mg/ml.

DPBS: Dulbeccos phosphate buffered saline, Sigma D8537

Lysis Buffer: 50 mM TRIS pH7.5+150 mM NaCl+1% Triton-X-100+2 mM EGTA+1:100 dilution inhibitor cocktails (phosphatase inhibitor cocktail set II, calbiochem cat no. 524625 & protease inhibitor cocktail set V, calbiochem cat no. 539137)

Triton-X-100: Roche 10 789 704 001 (GI 198233X, SC/159824). Made up as a 20% stock in water.

EGTA: Sigma E4378. Added solid directly to buffer.

2. B Cell Activity Assays 2.1. Ramos pErk Assay

Principle of the Assay

Ramos B cells (human B cells of Burkitt's Lymphoma) are stimulated using anti-IgM. This results in the recruitment of Syk to the B cell receptor. The subsequent autophosphorylation of Syk leads to initiation of a signalling cascade resulting in B cell activation via the Erk MAP Kinase pathway. As a result Erk is phosphorylated and following cell lysis is detected by an immune capture assay.

Stimulation of Ramos Cells with Anti-IgM

Cells were plated at a density of 2.5×10$^5$/well in a volume of 25 μl assay medium (RPMI containing 10% heat inactivated foetal calf serum, 1% L-glutamine) in 96 v-well polypropylene plates. 25 μl appropriately diluted compound solution was added and the plate incubated for 30 min at 37° C. with 5% CO$_2$. Cells were stimulated with 5 μl Fab'$_2$ fragments of goat anti-human IgM (5 μg/ml final) for 7 min at 37° C. Cells are lysed by the addition of 55 μL 2×RIPA lysis buffer for 2 h at 4° C. Lysate may be frozen at this point at −80° C.

pErk MSD Assay

50 μl cell lysate was transferred to a 96 well MSD plate coated with anti-pErk1/2 (Thr/Tyr:202/204; 185/187) capture antibody and incubated for 16 hours at 4° C. or 3 hours at room temperature. The plate was washed and an anti-pErk detection antibody added (25 μl/well) for 1 hour at room temperature. This was removed, 150 μL MSD read buffer added and the resultant electrochemiluminescence signal measured.

Compound Preparation

Compound was prepared as a 10 mM stock in DMSO and a dilution series prepared in DMSO using 9 successive 5-fold dilutions. This dilution series was diluted a further 1:100 with assay medium to give the final concentration range to be tested of 5×10$^{-5}$ to 2.56×10$^{-11}$M. Compound dilutions were prepared using the Biomek 2000 and Biomek Nx automated robotic pipetting systems.

The compounds of Examples 1, 2, 3 and 4 (as the hydrochloride salts) were tested essentially as described above and were each found to have an average IC$_{50}$ value in this assay of <1 μM.

The compounds of Examples 1, 2, 3 and 4 (as the hydrochloride salts) were tested essentially as described above and were each found to have an average pIC$_{50}$ value in this assay of ≥6.5. For example, Examples 1, 2, 3 and 4 (as the hydrochloride salts) were found to have average values of 7.4 (n=2), 7.2 (n=4), 7.0 (n=2) and 7.5 (n=4) respectively.

Those skilled in the art will recognize that in vitro binding assays and cell-based assays for functional activity are subject to variability. Accordingly, it is to be understood that the values for the IC$_{50}$s and pIC$_{50}$s recited above are exemplary only.

2.2 CD69 Whole Blood Assay

Principle of the Assay

Whole blood B cells are stimulated ex-vivo using anti-IgM. This results in the recruitment of Syk to the B cell receptor.

The subsequent autophosphorylation of Syk leads to initiation of a signalling cascade resulting in B cell activation as indicated by expression of the activation marker CD69 on the cell surface. CD20/CD69+ve whole blood B cells are detected by flow cytometry.

Stimulation of Whole Blood B Cells with Anti-IgM

100 μl heparinised human blood was added to a 5 ml polypropylene tube containing 1 μl appropriately diluted compound solution and incubated for 25 min at 37° C. with 5% $CO_2$. B cells were stimulated with 10 μl Fab'$_2$ fragments of goat anti-human IgM (43 μg/ml final concentration) for a further 3.5 h under the conditions previously described. The red blood cells were lysed and all other cells fixed by the addition of 2 ml Lyse/Fix buffer for 10 min at room temperature.

CD69 Assay

The cells were stained using a cocktail of mouse anti-human CD20 FITC and mouse anti-human CD69 PE conjugated antibodies. CD20/CD69+ve B cells present in the sample were detected by flow cytometry.

Compound Preparation

Compound was prepared as a 10 mM stock in DMSO, further diluted down in DMSO to 1 mM and a dilution series prepared in DMSO using 7 successive 3-fold dilutions to give the final concentration range to be tested of $1\times10^{-5}$ to $4.57\times10^{-9}$M. Compound dilutions were prepared using the Biomek 2000 automated robotic pipetting system.

The compounds of Examples 1, 2, 3, 4, 7, 8, 9A, 9B, 10, 11A and 11B (as the free base) were tested essentially as described above and were each found to have an average $IC_{50}$ value in this assay of <1 μM. The hydrochloric acid salts of compounds of Examples 1, 2, 3, 4 and 6 were tested essentially as described above and were each found to have an average $IC_{50}$ value in this assay of <1 μM.

The compounds of Examples 1, 2, 3, 4, 5, 7, 8, 9A, 9B, 10, 11A and 11B (as the free base) were tested essentially as described above and were each found to have an average $pIC_{50}$ value in this assay of ≥6.0. For example, Examples 1, 2, 3 and 4 (as the free base) were found to have average values of 6.5 (n=2), 6.8 (n=2), 6.6 (n=2) and 6.8 (n=2) respectively. The hydrochloric acid salts of compounds of Examples 1, 2, 3, 4 and 6 were tested essentially as described above and were each found to have an average $pIC_{50}$ value in this assay of ≥6.0.

Those skilled in the art will recognize that in vitro binding assays and cell-based assays for functional activity are subject to variability. Accordingly, it is to be understood that the values for the $IC_{50}$s and $pIC_{50}$s recited above are exemplary only.

3. hERG Activity—Cy3B Dofetilide Fluoro-Ligand Binding Assay for hERG

Compound potencies were determined by a fluoro-ligand§ (Cy3b-Dofetilide) fluorescence polarisation assay.

hERG-expressing CHO-K1 membranes* (60 μg/ml) were incubated with 1.0 nM fluoro-ligand§, in assay buffer (25 mM HEPES, 1.2 mM $MgCl_2$, 100 mM KCl and 0.1% pluronic, pH adjusted to 7.4 using 5M KOH). The final potassium concentration in the assay was 100 mM. After 70 min mixing at room temperature, in the dark, 10 μl was dispensed into each well of a black LV Greiner 384-well plate containing 0.1 μl of test compound in DMSO. The plates were left to equilibrate for 2 h before reading on an Acquest™/Analyst™ imager. $pIC_{50}$ data were generated using from an 11-point inhibition curve (top assay concentration of 50 μM and a 1:3 step-dilution), a six parameter curve-fit being applied using ABase and XC50 to analyse data and generate curve fits.

The compounds of Examples 1, 2, 3, 4, 5, 7, 8, 9A, 9B, 10, 11A and 11B (as the free base) were tested essentially as described above and were each found to have an average $IC_{50}$ value in this assay of greater than 10 μM. The hydrochloric acid salts of compounds of Examples 1, 2, 3, 4 and 6 were tested essentially as described above and were each found to have an average $IC_{50}$ value in this assay of greater than 20 μM.

The compounds of Examples 1, 2, 3, 4, 5, 7, 8, 9A, 9B, 10, 11A and 11B were tested essentially as described above and were each found to have an average $pIC_{50}$ value in this assay of less than 5.0. The hydrochloric acid salts of compounds of Examples 1, 2, 3, 4 and 6 were tested essentially as described above and were each found to have an average $pIC_{50}$ value in this assay of less than 5.0.

Those skilled in the art will recognize that in vitro binding assays and cell-based assays for functional activity are subject to variability. Accordingly, it is to be understood that the values for the $IC_{50}$s and $pIC_{50}$s recited above are exemplary only.

*CHO-K1 Membranes

Chinese Hamster Ovary (CHO) cells stably expressing the human hERG receptor were grown to 80% confluency before being harvested by trypsinisation and subsequent centrifugation at 500 g for 10 min. Cell pellets were frozen at −80 C before membrane production. The frozen pellet was thawed on ice, re-suspended and homogenised in 10 volumes of membrane buffer (50 mM HEPES, pH 7.4, 1 mM EDTA, 1 mM PMSF, $2\times10$-6M Pepstatin A). The membrane suspension was centrifuged for 20 min at 500 g, the pellet discarded and the supernatent spun again at 48,000 g for 30 min. Following the second centrifugation the remaining pellet containing the membrane fraction was re-suspended in an appropriate volume (4 ml for each ml of frozen cell pellet) and assayed for protein concentration.

§Fluoro-ligand (octahydrobenzo[2",3"]indolizino[8", 7":5',6']pyrano[3',2':3,4]pyrido[1,2-a]indol-5-ium-2-sulfonate (International Application no. PCT/EP2010/050228, publication no. WO2010/097248A1 (Glaxo Group Ltd), TFA salt described in J.M.C. 2007, 50(13), 2931-2941).

N-[4-({2-[(6-aminohexyl)(2-{4-[(methylsulfonyl)amino] phenyl}ethyl)amino]ethyl}oxy)phenyl]methanesulfonamide (1.508 mg) as a solution in acetonitrile (100 μl) was added to solid Cy3B-ONSu (14-{2-[(2,5-dioxo-1-pyrrolidinyl)oxy]-2-oxoethyl}-16,16,18,18-tetramethyl-6,7,7a,8a,9, 10,16,18-octahydrobenzo[2",3"]indolizino[8",7":5',6'] pyrano[3',2':3,4]pyrido[1,2-a]indol-5-ium-2-sulfonate (1.7 mg, WO9931181) in a silanised 4 ml vial. A second portion of acetonitrile (100 μl) was added followed by Hunig's base (0.9 μl). Two portions (2×50 μl) of dimethylformamide were added and the reaction mixture was concentrated under reduced pressure. The residue was re-dissolved in dimethylformamide (200 μl). Hunig's base (0.9 μl) was added and the mixture vortex mixed for 22 h. The reaction mixture was evaporated to dryness, re-dissolved in acetonitrile/water/acetic acid (5/4/1, ~500 μl), filtered and applied to a semi-preparative Spherisorb ODS2 HPLC column which was eluted with the following gradient (flow rate=5 ml/min, AU 5.0, 214 nm, AU 2, 256 nm, A=0.1% TFA/water, B=90% acetonitrile/ 10% water/0.1% TFA): t=0 min: B=5%; t=10 min: B=5%; t=30 min: B=25%; t=90 min: B=55%; t=105 min: B=100%; t=120 min: B=100%. The major component eluted between 46% and 48% B and collected in one fraction which was evaporated to dryness and the purple solid transferred to a vial using methanol as solvent. The methanol was removed under reduced pressure and the purple solid triturated with dry ether. The solid was dried overnight at 1 mbar in a drying pistol to give the title compound (1.2 mg).

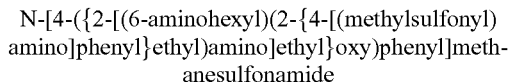

N-[4-({2-[(6-aminohexyl)(2-{4-[(methylsulfonyl)amino]phenyl}ethyl)amino]ethyl}oxy)phenyl]methanesulfonamide Crude N-[4-({2-[[6-(1,3-dioxo-1,3-dihydro-2H-isoindol-2-yl)hexyl](2-{4-[(methylsulfonyl)amino]phenyl}ethyl)amino]ethyl}oxy)phenyl]methanesulfonamide (142 mg) was dissolved in methylamine (33% in ethanol, 10 ml, 0.216) and left at 22° C. for 48 h. Excess reagent was evaporated under reduced pressure and the oily residue azeotroped with two further portions of ethanol. The crude product was dissolved in acetonitrile/water/acetic acid (5/4/, <2 ml), half applied to a Phenomenex Jupiter C18 HPLC column and eluted using the following gradient (flow rate=10 ml/min, AU 20.0, 214 nm, AU 10, 256 nm, A=0.1% TFA/water, B=90% acetonitrile/10% water/0.1% TFA): t=0 min: B=5%; t=10 min: B=5%; t=100 min: B=35%; t=115 min: B=100%; t=130 min: B=100%. Fractions containing mainly the slower eluting component (>90%) were pooled and evaporated to give the title compound (14.9 mg). The remaining crude was applied to the C18 column but with a modified gradient: t=0 min: B=5%; t=10 min: B=5%; t=15 min: B=10%; t=95 min: B=30%; t=110 min: B=100%; t=125 min: B=100%. Fractions containing mainly the desired product were combined and evaporated as before to yield the title compound (21.3 mg~80% purity). The material was used without further purification.

N-[4-({2-[[6-(1,3-dioxo-1,3-dihydro-2H-isoindol-2-yl)hexyl](2-{4-[(methylsulfonyl)amino]phenyl}ethyl)amino]ethyl}oxy)phenyl]methanesulfonamide 2-[6-([2-(4-aminophenyl)ethyl]{2-[(4-aminophenyl)oxy]ethyl}amino)hexyl]-1H-isoindole-1,3(2H)-dione (108.3 mg) was dissolved in DCM (5 ml) and cooled to 0-4° C. in an ice-bath. Hunig's Base (0.227 ml) was added followed by the dropwise addition of mesylchloride (0.051 ml). The reaction was maintained at 0-4° C. for 0.5 h and then allowed to warm slowly to room temperature. After 3 h the reaction mixture was evaporated to dryness and used crude in next step.

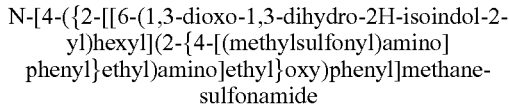

2-[6-([2-(4-aminophenyl)ethyl]{2-[(4-aminophenyl)oxy]ethyl}amino)hexyl]-1H-isoindole-1,3(2H)-dione 2-[6-([2-(4-nitrophenyl)ethyl]{2-[(4-nitrophenyl)oxy]ethyl}amino)hexyl]-1H-isoindole-1,3(2H)-dione (0.35 g) was dissolved in a mixture of ethanol (40 ml), water (5 ml) and acetic acid (5 ml) and the resulting solution degassed under reduced pressure. 10% Palladium on carbon (56% paste, 0.27 g) was added and the resulting mixture stirred vigorously under a hydrogen atmosphere (atmospheric pressure) for 12 h. The reaction mixture was filtered through Celite™ and washed with ethanol. The filtrate and washings were evaporated to dryness to give the title compound (0.313 g) which was used without further purification.

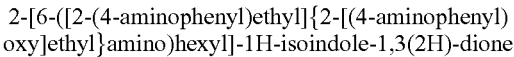

2-[6-([2-(4-nitrophenyl)ethyl]{2-[(4-nitrophenyl)oxy]ethyl}amino)hexyl]-1H-isoindole-1,3(2H)-dione

[2-(4-Nitrophenyl)ethyl]{2-[(4-nitrophenyl)oxy]ethyl}amine (253 mg) and 2-(6-bromohexyl)-1H-isoindole-1,3(2H)-dione (1186 mg) were dissolved in DMF (4 ml) and basified by the addition of DIPEA (0.665 ml). The reaction was stirred for 120 h. The reaction mixture was evaporated to dryness and the residue dissolved in DCM, the solution was absorbed onto a pad of silica and purified on a silica cartridge (12 g) eluting with the following gradient: (A=DCM, B=methanol) t=0 min: B=10%; t=7.5 min: B=0%; t=22.5 min: B=5%. The desired product eluted at ~15% B (isocratically) and evaporation of the solution to dryness gave the title compound (0.364 g).

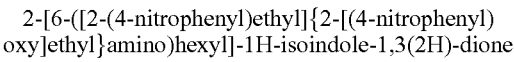

[2-(4-nitrophenyl)ethyl]{2-[(4-nitrophenyl)oxy]ethyl}amine

[[2-(4-nitrophenyl)ethyl]amine (498.9 mg) and 111-[(2-bromoethyl)oxy]-4-nitrobenzene 2-bromoethyl 4-nitrophenyl ether (513 mg) were dissolved in DMF (5 ml) at 22° C. and DIPEA (0.872 ml) added. The reaction mixture was left for 60 h at 22° C., evaporated to dryness and the residue dissolved in DCM. The compound was absorbed onto silica and purified on a silica cartridge (12 g) in two batches eluting with a methanol/DCM gradient (0-15%). Fractions containing pure product were pooled and the solvent removed under reduced pressure. The resulting title compound was isolated as a deep yellow oil which partially solidified under high vacuum (253 mg).

4. Bacterial Mutation Screening Assay (Ames Test)

The bacterial mutation assay (Ames Test) is a short-term reverse mutation assay specifically designed to detect a wide range of chemical substances that can produce genetic damage that leads to gene mutations (base pair substitutions and frameshift mutations).

The test employs several histidine dependent *Salmonella typhimurium* strains and several tryptophan dependent strains of *Escherichia coli* each carrying different mutations in various genes in the histidine or tryptophan operon respectively. These mutations act as hot spots for mutagens that cause DNA damage via different mechanisms.

Briefly, bacteria are cultured for 10 h prior to the test. Top agar is supplemented with trace amounts of histidine, biotin, and tryptophan and aliquoted, before adding the required test article, vehicle or positive control followed by the appropriate bacterial suspension, and either an exogenous mammalian oxidative metabolism system (S9-mix) or buffer solution. The final mixture is poured over minimal agar plates which are then inverted and incubated before scoring for revertant colonies.

When the tester strains are grown on a minimal media agar plate containing a trace of histidine or tryptophan, only those bacteria that revert to histidine or tryptophan independence are able to form colonies. The number of spontaneously induced revertant colonies per plate is relatively constant. However, when a mutagen is added to the plate, the number of revertant colonies per plate is increased, usually in a dose-related manner.

Bacterial Strains routinely used are *Salmonella typhimurium* strains TA98, TA100 TA1535 and TA1537 and *Escherichia coli* WP2 uvrA (pKM101).

Assays are performed in the presence and absence of an exogenous mammalian oxidative metabolising system (S9-mix), to mimic mammalian metabolism.

The highest concentration tested is one that allows maximum exposure up to 5000 µg/plate for freely soluble compounds, or the limit of solubility or toxicity (whichever is the lower). If compound solubility is a limiting factor, the maximum concentration chosen will be the lowest concentration at which compound precipitate is observed by eye on treatment plates at the end of the incubation period.

Appropriate vehicle and positive controls are included in all tests.

A single mutation assay (using the plate incorporation methodology) is conducted in the presence and absence of S9-mix (consisting of 4 replicate plates for vehicle controls and 2 replicate plates for the positive controls and test article).

Plates are usually scored electronically for bacterial colony formation following inspection of the plates for signs of toxicity (i.e. reduced growth (diminution) of background lawn, the presence of pin-dot/pseudorevertant colonies and/or a reduction in colony numbers). Plates will also be evaluated (by eye) for compound precipitation. Where compound precipitation occurs, scoring of bacterial colony formation for each strain will stop at the lowest treatment concentration at which compound precipitate is observed on the test plates at the end of the incubation period.

The number of colonies on each plate is recorded and mean values calculated for each concentration of test article used. Mean values are also be expressed as a ratio of the mean concurrent vehicle control value (i.e. fold increase). In addition, any observed precipitate or toxicity are documented.

If the data for any treatment level shows a response ≥2 times the concurrent vehicle control value (TA98, TA100 TA102 WP2 uvrA (pKM101) and WP2 (pKM101)), or times the concurrent vehicle control value (TA1535 and TA1537), in conjunction with a dose related response, the result is considered positive.

Where the data for any strain shows a dose related response, approaching the 2 or 3 fold threshold as detailed above, but does not exceed it, the result is considered equivocal and further testing may be required for clarification The test methodology is based on established procedures for bacterial mutagenicity testing [Maron, 1983; Green, 1984; Ames, 1975; Garner, 1972; Green, 1976; Ames, 1973] and is in accordance with the general principles of the following regulatory guidelines.

The compounds of Examples 1, 2, 3 and 4 (as the free base) were negative in this assay.

COM (2000) Guidance on a Strategy for Testing of Chemicals for Mutagenicity, Committee on Mutagenicity of Chemicals in Food, Consumer Products and the Environment, December 2000.

ICH-S2A (1996) "Specific Aspects of Regulatory Genotoxicity Tests for Pharmaceuticals", in: Federal Register, April 1996 (61 FR 18199).

ICH-S2B (1997) "A Standard Battery for Genotoxicity Testing of Pharmaceuticals", in: Federal Register, November 1997 (62 FR 62472).

Gatehouse, D. G., Wilcox, P., Forster, R., Rowland, I. R. and Callander, R. D. (1990) Bacterial Mutation Assays. In: D. J. Kirkland (Ed.), Basic Mutagenicity Test: UKEMS Recommended Procedures. Cambridge University Press, Cambridge, UK, pp. 13 61.

OECD (1997) "Bacterial Reverse Mutation Test", in: OECD Guideline for the Testing of Chemicals, Test Guideline 471.

INTERMEDIATES AND EXAMPLES

General

All temperatures are in ° C.
Bis(pinacolato)diboron refers to 4,4,4',4',5,5,5',5'-octamethyl-2,2'-bi-1,3,2-dioxaborolane
$BH_3$.DMS refers to borane dimethylsulphide complex
$BH_3$-THF refers to borane tetrahydrofuran complex
BINAP refers to 2,2'-bis(diphenylphosphino)-1,1'-binapthyl
[(S)BINAP]Pd(OTf)$_2$ refers to (S)-2,2'-bis(diphenylphosphino)-1,1'-binapthyl bis(acetonitrile)palladium (II) triflate
BOC refers to tert-butoxycarbonyl
$BOC_2O$ refers to Di-tert-butyl dicarbonate
BuOH refers to butanol
tert-BuOK refers to potassium tert-butoxide
n-BuOAc refers to n-butyl acetate
$ClCO_2Et$ refers to ethyl chloroformate
$Cs_2CO_3$ refers to caesium carbonate
$Cu(OAc)_2$ refers to cooper acetate
CV refers to column volume
DCM refers to dichloromethane
DIPEA refers to N,N-diisopropylethylamine
DMAP refers to 4-dimethylaminopyridine
DME refers to dimethoxyethane
DMSO refers to dimethylsulfoxide.
DMF refers to N,N-dimethylformamide
$Et_3N$ refers to triethylamine
$Et_2O$ or Ether refers to diethyl ether
EtOAc refers to ethyl acetate
EtOH refers to ethanol
FMOC refers to 9-fluorenylmethyloxycarbonyl
h refers to hours
HCl refers to hydrochloric acid
$H_2O$ refers to water
HPLC refers to high performance liquid chromatography
IPA refers to iso-propanol
$K_2CO_3$ refers to potassium carbonate
KOAc refers to potassium acetate
KOH refers to potassium hydroxide
LCMS refers to liquid chromatography-mass spectroscopy
MDAP refers to mass directed autoprep
$Me_4NCl$ refers to tetramethylammonium chloride
MeOD refers to deuterated methanol
min refers to minutes
nBuLi refers to N-butyllithium
NBS refers to N-bromosuccinimide
$NaHCO_3$ refers to sodium bicarbonate
$Na_2SO_4$ refers to sodium sulfate
$NaN_3$ refers to sodium azide
NMP refers to N-methylpyrrolidone
$(PhSO_2)_2NF$ or NFSI refers to N-fluorobenzenesulfonimide
Pd/C refers to palladium on carbon
$PdCl_2$.dppf refers to [1,1'-bis(diphenylphosphino)ferrocene]dichloropalladium
$Pd_2(dba)_3$ refers to tris(dibenzylideneacetone)dipalladium (0)
$Pd(PPh_3)_4$ refers to tetrakis(triphenylphosphine) palladium (0)
$Pd(di-t-bpf)Cl_2$ refers to 1,1'-bis(di-tert-butylphosphino)ferrocene palladium dichloride
PEPPSI refers to Pyridine-Enhanced Precatalyst Preparation Stabilization and Initiation
$POCl_3$ refers to phosphorus oxychloride
Pt/C refers to platinum on carbon
r.t. refers to room temperature
Rt refers to retention time
TBME refers to tert-butyl methyl ether
TEA refers to triethylamine
TFA refers to trifluoroacetic acid
$Tf_2O$ refers to triflic anhydride
THF refers to tetrahydrofuran
$^1H$ NMR spectra were recorded using a Bruker DPX 400 MHz, referenced to tetramethylsilane.

LC/MS (Method A) was conducted on an Acquity HPLC BEH C18 column (50 mm×2.1 mm i.d. 1.7 μm packing diameter) at 40 degrees centigrade, eluting with 10 mM ammonium bicarbonate in water adjusted to pH 10 with ammonia solution (Solvent A) and acetonitrile (Solvent B) using the following elution gradient 0-1.5 min 1-97% B, 1.5-1.9 min 97% B, 1.9-2.0 min 100% B at a flow rate of 1 ml/min. The UV detection was a summed signal from wavelength of 210 nm to 350 nm. The mass spectra were recorded on a Waters ZQ Mass Spectrometer using Alternate-scan Positive and Negative Electrospray. Ionisation data was rounded to the nearest integer.

LC/MS (Method B) was conducted on an Acquity HPLC BEH C18 column (50 mm×2.1 mm i.d. 1.7 μm packing diameter) at 40 degrees centigrade, eluting with 0.1% v/v solution of formic Acid in water (Solvent A) and 0.1% v/v solution of formic acid in acetonitrile (Solvent B) using the following elution gradient 0-1.5 min 3-100% B, 1.5-1.9 min 100% B, 1.9-2.0 min 3% B at a flow rate of 1 ml/min. The UV detection was a summed signal from wavelength of 210 nm to 350 nm. The mass spectra were recorded on a Waters ZQ Mass Spectrometer using Alternate-scan Positive and Negative Electrospray. Ionisation data was rounded to the nearest integer.

LC/MS (Method C) was conducted on an Acquity HPLC BEH C18 column (50 mm×2.1 mm i.d. 1.7 μm packing diameter) at 40 degrees centigrade, eluting with 0.1% v/v solution of trifluoroacetic acid in water (Solvent A) and 0.1% v/v solution of trifluoroacetic acid in acetonitrile (Solvent B) using the following elution gradient 0-1.5 min 3-100% B, 1.5-1.9 min 100% B, 1.9-2.0 min 3% B at a flow rate of 1 ml/min. The UV detection was a summed signal from wavelength of 210 nm to 350 nm. The mass spectra were recorded on a Waters ZQ Mass Spectrometer using Alternate-scan Positive and Negative Electrospray. Ionisation data was rounded to the nearest integer.

MDAP (Method A). The HPLC analysis was conducted on an XBridge O18 column (100 mm×30 mm i.d. 5 μm packing diameter) at ambient temperature, eluting with 10 mM ammonium bicarbonate in water adjusted to pH 10 with ammonia solution (Solvent A) and acetonitrile (Solvent B) using the following elution gradient:

| Time (min) | Flow Rate (ml/min) | % A | % B |
| --- | --- | --- | --- |
| 0 | 40 | 85 | 15 |
| 1 | 40 | 85 | 15 |
| 10 | 40 | 45 | 55 |
| 11 | 40 | 1 | 99 |
| 15 | 40 | 1 | 99 |

The UV detection was an averaged signal from wavelength of 210 nm to 350 nm. The mass spectra were recorded on a Waters ZQ Mass Spectrometer using Alternate-scan Positive and Negative Electrospray. Ionisation data was rounded to the nearest integer.

MDAP (Method B). The HPLC analysis was conducted on an XBridge O18 column (100 mm×30 mm i.d. 5 μm packing diameter) at ambient temperature, eluting with 10 mM ammonium bicarbonate in water adjusted to pH 10 with ammonia solution (Solvent A) and acetonitrile (Solvent B) using the following elution gradient:

| Time (min) | Flow Rate (ml/min) | % A | % B |
| --- | --- | --- | --- |
| 0 | 40 | 85 | 15 |
| 1 | 40 | 85 | 15 |
| 20 | 40 | 45 | 55 |
| 21 | 40 | 1 | 99 |
| 25 | 40 | 1 | 99 |

The UV detection was an averaged signal from wavelength of 210 nm to 350 nm. The mass spectra were recorded on a Waters ZQ Mass Spectrometer using Alternate-scan Positive and Negative Electrospray. Ionisation data was rounded to the nearest integer.

MDAP (Method C). The HPLC analysis was conducted on a Sunfire O18 column (150 mm×30 mm i.d. 5 μm packing diameter) at ambient temperature, eluting with 0.1% v/v solution of trifluoroacetic acid in water (Solvent A) and 0.1% v/v solution of trifluoroacetic acid in acetonitrile (Solvent B) using the following elution gradient:

| Time (min) | Flow Rate (ml/min) | % A | % B |
| --- | --- | --- | --- |
| 0 | 40 | 100 | 0 |
| 3 | 40 | 100 | 0 |
| 3.5 | 30 | 100 | 0 |
| 24.5 | 30 | 70 | 30 |
| 25 | 30 | 1 | 99 |
| 32 | 30 | 1 | 99 |

The UV detection was an averaged signal from wavelength of 210 nm to 350 nm. The mass spectra were recorded on a Waters ZQ Mass Spectrometer using Alternate-scan Positive and Negative Electrospray. Ionisation data was rounded to the nearest integer.

MDAP (Method D). The HPLC analysis was conducted on a Sunfire O18 column (150 mm×30 mm i.d. 5 μm packing diameter) at ambient temperature, eluting with 10 mM ammonium bicarbonate in water adjusted to pH 10 with ammonia solution (Solvent A) and acetonitrile (Solvent B) using the following elution gradient:

| Time (min) | Flow Rate (ml/min) | % A | % B |
| --- | --- | --- | --- |
| 0 | 40 | 100 | 0 |
| 3 | 40 | 100 | 0 |
| 3.5 | 30 | 100 | 0 |
| 24.5 | 30 | 70 | 30 |
| 25 | 30 | 1 | 99 |
| 32 | 30 | 1 | 99 |

The UV detection was an averaged signal from wavelength of 210 nm to 350 nm. The mass spectra were recorded on a Waters ZQ Mass Spectrometer using Alternate-scan Positive and Negative Electrospray. Ionisation data was rounded to the nearest integer.

Silica chromatography techniques include either automated (Flashmaster, Biotage SP4) techniques or manual chromatography on pre-packed cartridges (SPE) or manually-packed flash columns.

When the name of a commercial supplier is given after the name of a compound or a reagent, for instance "compound X (Aldrich)" or "compound X/Aldrich", this means that compound X is obtainable from a commercial supplier, such as the commercial supplier named.

Similarly, when a literature or a patent reference is given after the name of a compound, for instance compound Y (EP 0 123 456), this means that the preparation of the compound is described in the named reference.

The names of the above mentioned Examples have been obtained using the compound naming programme "ACD Name Pro 6.02".

Intermediate 1: Ethyl (3S)-3-fluoro-2-oxo-3-piperidinecarboxylate

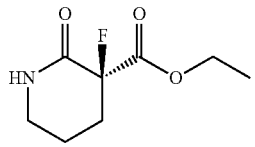

2,6-Lutidine (31.7 g, 296 mmol) (Aldrich) was added drop wise over 30 min to a suspension of ethyl 2-oxo-3-piperidinecarboxylate (101.2 g, 591 mmol) (Aldrich), [(S)-(−)-2,2'-bisphosphino)-1,1'-binaphthyl]palladium (II) dihydrate ditriflate (3.14 g, 2.96 mmol) (Sodeoka, M et al. *Synlett* 1997, 463-466; Fujii, A et al. *J. Am. Chem. Soc.* 1999, 121, 5450-5458) (Aldrich) and N-fluorobenzenesulfonimide (242.0 g, 768 mmol) (Aldrich) in ethanol (500 ml) at 0° C. in an ice bath. The temperature was maintained at approximately 10° C. during addition and then allowed to warm to room temperature overnight as ice melted. Presence of solid around flask (3 L) neck suggests possible exotherm may have occurred overnight. LCMS showed presence of product. The reaction was filtered and the solid was washed with ethanol, then DCM (200 ml). NMR confirmed no product in solid. The liquors were evaporated and re-dissolved in DCM (3500 ml). The organics were washed with saturated ammonium chloride solution (300 ml) and the aqueous was re-extracted with DCM (2×200 ml). The combined organics were evaporated and re-dissolved in DCM (300 ml), filtered through celite and washed with DCM (200 ml). The organic solution was left to stand overnight (sealed so no evaporation)—a fine precipitate appeared. The mixture was filtered through celite again and washed with DCM.

The combined organic layers were loaded onto a 1500 g silica column and purified on the companion XL eluting with 0-100% ethyl acetate in cyclohexane gradient. Appropriate fractions were identified by LCMS, combined and the solvent was removed to give the title compound as a yellow solid, which was dried under high vacuum for 1 h (92.2 g).

LCMS (Method B): Rt=0.52 min, MH⁺ 190

Chiral analytical HPLC (25 cm Chiralpak IA, col. no. IAOOCE-MC024, 15% EtOH/C7, 1 ml/min, wavelength 215 nm, RT) showed enrichment of the fast eluter—44% ee. The compound was combined with three other batches of varying enantiomeric enrichment and 215 g of material was purified further using preparative HPLC to improve the enantiomeric excess of the fast eluter to >99%.

Samples were prepared in batches according to the following method: ethyl-3-fluoro-2-oxo-3-piperidinecarboxylate (25 g) was dissolved in ethanol (450 ml) with gentle heating and sonication. The solution was then filtered through a Pall Acrodisc 37 mm syringe filter with 1 µm glass fibre membrane to remove fines and undissolved material. The filtered solution was adjusted to a total volume of 500 ml with ethanol to give a solution with nominal concentration of 50 mg/mL.

The preparative HPLC details were as follows:

| | |
|---|---|
| Column | Chiralpak AD, 330 × 50 mm, 20 µm |
| Mobile Phase | A: Heptane B: Ethanol |
| Gradient Profile | 15% B Isocratic |
| Run Time | 20 min |
| Flow Rate | 473 mL/min |
| Column Temperature | 20° C. |
| Wavelength | 220 nm |

Intermediate 2: 1,1-Dimethylethyl (3S)-3-fluoro-3-(hydroxymethyl)-1-piperidinecarboxylate

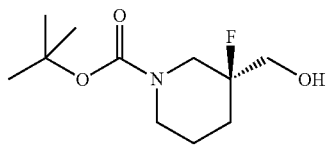 [SMILES: CC(C)(C)OC(=O)N1CCC[C@@](F)(CO)C1]

Ethyl (3S)-3-fluoro-2-oxo-3-piperidinecarboxylate (50 g, 264 mmol) was dissolved in THF (100 ml) and borane-THF complex (793 ml, 793 mmol, 1M solution) was added drop wise. The mixture was heated at reflux for 24 h, cooled to room temperature and the borane quenched by addition of methanol (150 ml). 2M HCl (200 ml) was added and the mixture heated to reflux for 20 min, then cooled and evaporated in vacuo. The residue was suspended in DCM (500 ml) and triethylamine (111 ml, 793 mmol) was added, followed by BOC anhydride (73.6 ml, 317 mmol). The mixture was stirred for 3 h, then washed with water (100 ml) and 0.5M HCl (100 ml), dried and evaporated to give 1,1-dimethylethyl (3S)-3-fluoro-3-(hydroxymethyl)-1-piperidinecarboxylate as pale yellow crystalline solid (52.85 g).

LCMS (Method B): Rt=0.80 min, MH⁺ 234

Intermediate 3: 1,1-dimethylethyl (3S)-3-fluoro-3-({[(trifluoromethyl)sulfonyl]oxy}methyl)-1-piperidinecarboxylate

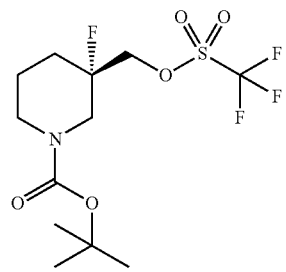 [SMILES: CC(C)(C)OC(=O)N1CCC[C@@](F)(COS(=O)(=O)C(F)(F)F)C1]

Triflic anhydride (24.06 ml, 142 mmol) was added to a solution of 1,1-dimethylethyl (3S)-3-fluoro-3-(hydroxymethyl)-1-piperidinecarboxylate (30.2 g, 129 mmol) and triethylamine (23.46 ml, 168 mmol) in DCM (100 ml) at −10° C. over 20 min. The mixture was stirred for 2 h, allowing to warm to 0° C., then washed with water and brine, dried and evaporated to give 1,1-dimethylethyl (3S)-3-fluoro-3-({[(trifluoromethyl)sulfonyl]oxy}methyl)-1-piperidinecarboxylate as a dark brown oil (50.2 g).

LCMS (Method B): Rt=1.23 min, MH⁺ 366

Intermediate 4: 1,1-dimethylethyl (3S)-3-(azidomethyl)-3-fluoro-1-piperidinecarboxylate

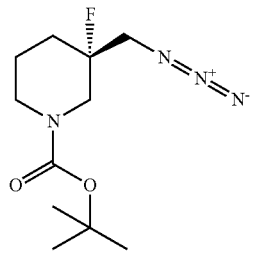 [SMILES: CC(C)(C)OC(=O)N1CCC[C@@](F)(CN=[N+]=[N-])C1]

Sodium azide (9.79 g, 151 mmol) was added to a solution of 1,1-dimethylethyl (3S)-3-fluoro-3-({[(trifluoromethyl)sulfonyl]oxy}methyl)-1-piperidinecarboxylate (50 g, 137 mmol) in DMF (200 ml) and the mixture was heated to 80° C. for 1 h. A sample was taken and quenched with water, extracted with ether and the ether layer evaporated in vacuo. The residue was analysed by NMR showing complete consumption of starting material.

The mixture was cooled, diluted with water (1 L) and extracted with EtOAc (2×300 ml). The solvent was washed with water (2×300 ml), dried and evaporated to give 1,1-dimethylethyl (3S)-3-(azidomethyl)-3-fluoro-1-piperidinecarboxylate as an amber oil (36.7 g).

LCMS (Method B): Rt=1.12 min, MH$^+$ 259

Intermediate 5: 1,1-Dimethylethyl (3R)-3-(aminomethyl)-3-fluoro-1-piperidinecarboxylate

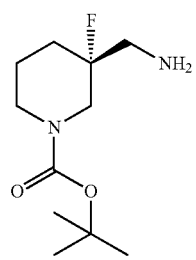 [SMILES: CC(C)(C)OC(=O)N1CCC[C@@](F)(CN)C1]

1,1-Dimethylethyl (3S)-3-(azidomethyl)-3-fluoro-1-piperidinecarboxylate (36 g, 139 mmol) was dissolved in ethanol (500 ml) and added under nitrogen to Pd/C (2.6 g, 1.222 mmol). The mixture was hydrogenated at atmospheric pressure overnight. The suspension was filtered and the filtrate evaporated in vacuo to give 1,1-dimethylethyl (3R)-3-(aminomethyl)-3-fluoro-1-piperidinecarboxylate as a pale yellow oil (32.7 g). $^1$H NMR (CDCl$_3$) 3.75-3.52 ppm (2H, 2×m, 2×CH), 3.30 ppm (1H, dd, CH), 3.20 ppm (1H, m, CH), 2.90-2.73 ppm (2H, m, CH$_2$), 1.96-1.72 ppm (2H, 2×m, CH$_2$), 1.70-1.58 ppm (1H, m, CH), 1.57-1.43 ppm (10H, m+s, CH+3×CH$_3$), 1.32 ppm (2H, br.s, NH$_2$).

Intermediate 6: N-(2,6-Dichloro-4-pyridinyl)-2,2-dimethylpropanamide

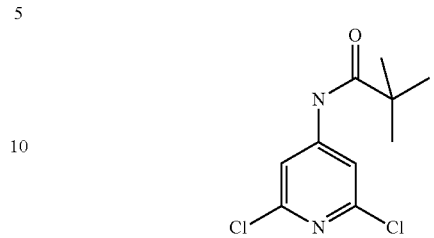

2,6-Dichloro-4-pyridinamine (10 g, 61.3 mmol) (Aldrich) and triethylamine (10.69 ml, 77 mmol) were combined in dichloromethane (DCM) (75 ml) and cooled in an ice-bath. 2,2-dimethylpropanoyl chloride (8.30 ml, 67.5 mmol) (Aldrich) in DCM (15 ml) was added drop wise and the mixture stirred whilst allowing to warm up overnight producing a clear dark orange solution. LCMS showed good conversion to product. The solution was washed with water and sat. NaHCO$_3$ (100 ml each), dried with Na$_2$SO$_4$, filtered and concentrated to yield a dark orange solid. The crude product was taken up in the minimum of DCM and applied to a 320 g Companion XL silica column and eluted with 0% EtOAc in cyclohexane for 2 CVs then 0-15% EtOAc in cyclohexane over 12 CVs then held at 15% for 2 CV. Appropriate fractions were combined and evaporated to give the title compound as a yellow solid (11.59 g).

LCMS (Method B): Rt=1.13 min, MH$^+$ 247/249

Intermediate 7: 5,7-Dichloro-1,6-naphthyridine

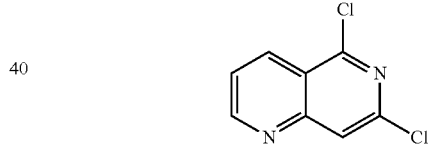

N-(2,6-Dichloro-4-pyridinyl)-2,2-dimethylpropanamide (1 g, 4.05 mmol) was taken up in THF (10 ml) under nitrogen and cooled to <−70° C. n-Butyl lithium (4.05 ml, 10.12 mmol, 2.5M solution in hexanes) was added over 30 min keeping the temperature below −60° C. and then stirred at below −70° C. for 1 h. (2E)-3-(dimethylamino)-2-propenal (0.607 ml, 6.07 mmol) in THF (2 ml) was added over 30 min keeping the temperature below −60° C. The reaction was stirred at below −70° C. for 20 min and then allowed to warm to room temperature. LCMS showed that no starting material remained so the reaction was quenched with 5M HCl (5 ml) and refluxed overnight. LCMS showed good conversion to product so the reaction was cooled to room temperature. The reaction mixture was basified with solid K$_2$CO$_3$ and extracted with EtOAc (4×25 ml). The combined organics were dried with Na$_2$SO$_4$, filtered and concentrated to yield a brown solid. The crude product was applied to a samplet and columned using a 40+M eluting with 12% diethyl ether in cyclohexane for 2 CVs, then with 12%-63% diethyl ether in cyclohexane over 10 CVs then held at 63% for 5CVs. Appropriate fractions were combined and evaporated to give the title compound as a yellow solid (0.42 g).

LCMS (Method B): Rt=0.89 min, MH$^+$ 199/201

Intermediate 8: 1,1-Dimethylethyl (3R)-3-{[(7-chloro-1,6-naphthyridin-5-yl)amino]methyl}-3-fluoro-1-piperidinecarboxylate

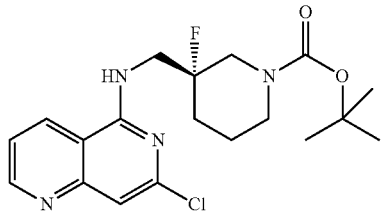 [SMILES: CC(C)(C)OC(=O)N1CCC[C@@](F)(CNc2nc(Cl)cc3ncccc23)C1]

To 5,7-dichloro-1,6-naphthyridine (5.01 g, 25.2 mmol) and 1,1-dimethylethyl (3R)-3-(aminomethyl)-3-fluoro-1-piperidinecarboxylate (5.32 g, 22.90 mmol) in NMP (20 ml) was added DIPEA (8.00 ml, 45.8 mmol) and the mixture was stirred at 100° C. for 72 h under nitrogen. The reaction was cooled and partitioned between ethyl acetate and water (200 ml each). The aqueous was washed with ethyl acetate. The combined organics were washed with water and the solvent was removed. The residue was dissolved in DCM and loaded onto a 100 g silica SNAP column and purified on the SP4 eluting with 0-50% ethyl acetate in cyclohexane over 17 CVs. Appropriate fractions were combined and the solvent was removed to give the title compound as a pale orange solid which was dried under high vacuum for 2 h (7.61 g).

LCMS (Method B): Rt=1.12 min, MH+ 395/397

Intermediate 9: 1-(1,1-Dimethylethyl)-1H-pyrazole

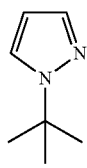

A mixture of (1,1-dimethylethyl)hydrazine hydrochloride (1.02 g, 8.19 mmol) (Aldrich), 1,1,3,3-tetrakis(methyloxy)propane (1.344 g, 8.19 mmol) (Aldrich) and hydrochloric acid (0.672 ml, 8.19 mmol) in ethanol (10 ml) was heated under reflux. A solution formed. After 16 h the reaction had gone to completion and so was concentrated in vacuo to yield the crude product. This was dissolved in methanol and passed through an aminopropyl cartridge (20 g), eluting with methanol. The combined filtrates were concentrated in vacuo to yield the title compound as a cream gum (210 mg)

LCMS (Method B): Rt=0.74 min, MH+=125.6

Intermediate 10: 4-Bromo-1-(1,1-dimethylethyl)-1H-pyrazole

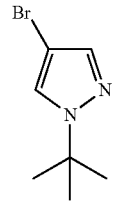

To an ice cooled solution of 1-(1,1-dimethylethyl)-1H-pyrazole (6.1 g, 49.1 mmol) in dichloromethane (DCM) (200 ml) was added N-bromosuccinimde (8.74 g, 49.1 mmol). This was warmed to ambient temperature and stirred for 18 h. There was no starting material present and so the reaction mixture was quenched with aqueous sodium thiosulfate. The organics were washed with water (2×500 ml) and passed through a hydrophobic frit. The filtrate was concentrated in vacuo to yield an orange-brown oil which turned purple on standing (7.402 g).

LCMS (Method B): Rt=1.03 min, MH+=203, 205

Intermediate 11: 1-(1,1-Dimethylethyl)-4-(4,4,5,5-tetramethyl-1,3,2-dioxaborolan-2-yl)-1H-pyrazole

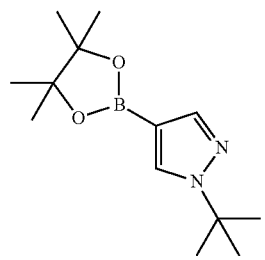 [SMILES: CC(C)(C)n1cc(B2OC(C)(C)C(C)(C)O2)cn1]

A mixture of 4-bromo-1-(1,1-dimethylethyl)-1H-pyrazole (2.4 g, 11.82 mmol), 4,4,4',4',5,5,5',5'-octamethyl-2,2'-bi-1,3,2-dioxaborolane (3.00 g, 11.82 mmol), potassium acetate (2.90 g, 29.5 mmol), tris(dibenzylideneacetone)dipalladium (0) (0.108 g, 0.118 mmol), 2-(dicyclohexylphosphino)-2',4',6'-triisopropylbiphenyl (0.225 g, 0.473 mmol) in 1,4-dioxane (30 ml) was degassed with nitrogen. The reaction mixture was spilt into 2 microwave vials and heated at 110° C. in a microwave for 1.5 h. There was no starting material remaining so the reactions were filtered through a bond elute reservoir and the residue was washed with ethyl acetate. The filtrate was concentrated in vacuo to yield the crude product. This was dissolved in DCM and purified through silica (50 g) eluting with 0-50% ethyl acetate in DCM gradient. Appropriate fractions were combined and concentrated in vacuo to yield the title compound as a beige solid (1.68 g).

LCMS (Method B): Rt=1.08 min, MH+=250.8

Intermediate 12: 1-[(Methyloxy)methyl]-4-(4,4,5,5-tetramethyl-1,3,2-dioxaborolan-2-yl)-1H-pyrazole

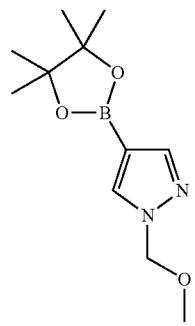

4-(4,4,5,5-Tetramethyl-1,3,2-dioxaborolan-2-yl)-1H-pyrazole (400 mg, 2.061 mmol) (Aldrich) was dissolved in acetonitrile (25 ml) and stirred for 5 min at 35° C. Iodomethyl methyl ether (0.873 ml, 10.31 mmol) and potassium carbonate (1424 mg, 10.31 mmol) were added and the mixture was allowed to stir at 35° C. for 3 h.

The LCMS showed incomplete reaction. The mixture was left to stir at 35° C. for one additional hour. The LCMS showed no progression so 2 eq (349 µl) of the alkylating agent was added and the mixture was allowed to stir at 35° C. for 30 min. Ammonium chloride was then added. The mixture was partitioned between ethyl acetate and water. The aqueous layer was re-extracted with ethyl acetate and the combined organic phases were washed with water, dried using a hydrophobic frit and concentrated to an oil. The oil was purified on 50 g silica using an SP4 and eluted with a 0-100% ethyl acetate/cyclohexane gradient. The product was found in the waste, which was concentrated to give the title compound as an oil (260 mg).

LCMS (Method B): Rt=0.84 min, MH$^+$=238.85

Intermediate 13: 1,1-Dimethylethyl (3R)-3-({[7-(1-ethyl-1H-pyrazol-4-yl)-1,6-naphthyridin-5-yl]amino}methyl)-3-fluoro-1-piperidinecarboxylate

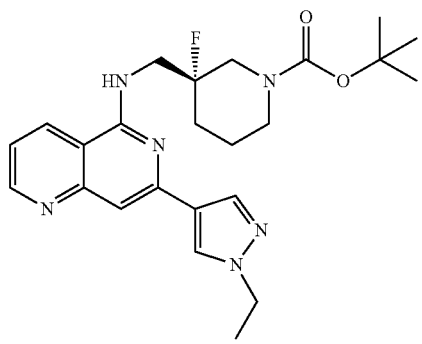 [SMILES: CCn1cc(-c2cc3ncccc3c(NC[C@]3(F)CCCN(C(=O)OC(C)(C)C)C3)n2)cn1]

To a 2-5 mL microwave vial under nitrogen was added caesium carbonate (990 mg, 3.04 mmol) and 1-ethyl-4-(4,4,5,5-tetramethyl-1,3,2-dioxaborolan-2-yl)-1H-pyrazole (292 mg, 1.317 mmol) (Boron Molecular). 1,1-Dimethylethyl (3R)-3-{[(7-chloro-1,6-naphthyridin-5-yl)amino]methyl}-3-fluoro-1-piperidinecarboxylate (400 mg, 1.013 mmol) was dissolved in 1,4-dioxane (4 ml) and water (0.8 ml) and added in one aliquot. Nitrogen was bubbled through the resultant suspension for ~2 min. Tetrakis(triphenylphosphine)palladium (0) (117 mg, 0.101 mmol) was then added in one portion and nitrogen bubbled through the yellow suspension for a further ~1 min. The microwave vial was sealed and heated at 150° C. in a microwave reactor for 1 h. LCMS showed the reaction had gone to completion. The reaction was partitioned between water (20 ml) and ethyl acetate (20 ml). The aqueous layer was further extracted with ethyl acetate (2×20 ml) and the combined organics washed with brine (10 ml). The organics were dried (Na$_2$SO$_4$) and concentrated in vacuo.

The reaction was repeated as above using the same amounts and reaction conditions. The two crude batches were combined and purified using a 100 g Biotage silica column and eluted with a 0-100% ethyl acetate/cyclohexane gradient. Appropriate fractions were combined and concentrated in vacuo to give the title compound as a colourless oil (811 mg)

LCMS (Method B): Rt=0.88 min, MH$^+$ 455

Intermediate 14: 1,1-Dimethylethyl (3R)-3-[({7-[1-(1,1-dimethylethyl)-1H-pyrazol-4-yl]-1,6-naphthyridin-5-yl}amino)methyl]-3-fluoro-1-piperidinecarboxylate

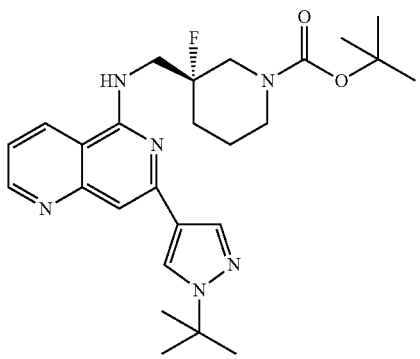 [SMILES: CC(C)(C)OC(=O)N1CCC[C@@](F)(CNc2nc(-c3cnn(C(C)(C)C)c3)cc3ncccc23)C1]

To a solution of 1,1-dimethylethyl (3R)-3-{[(7-chloro-1,6-naphthyridin-5-yl)amino]methyl}-3-fluoro-1-piperidinecarboxylate (1.300 g, 3.29 mmol) in 1,4-dioxane (10 ml) was added 1-(1,1-dimethylethyl)-4-(4,4,5,5-tetramethyl-1,3,2-dioxaborolan-2-yl)-1H-pyrazole (0.906 g, 3.62 mmol), caesium carbonate (2.145 g, 6.58 mmol), tetrakis(triphenylphosphine)palladium (0) (0.114 g, 0.099 mmol) and water (2 ml). The reaction mixture was heated in the microwave at 130° C. for 2 h. LCMS shows main peak of product with no starting material. The reaction mixture was filtered through 10 g celite and partitioned between ethyl acetate and water (100 ml×2). The organic layer was washed with brine (100 ml), evaporated the solvent and dissolved in minimum amount of DCM. This was loaded on to a 100 g silica column and purified on SP4 eluting with 20-90% ethyl acetate in cyclohexane over 22 CVs. Appropriate fractions were collected and the solvent was evaporated. The product was dried on high vacuum overnight to give the title compound as a yellow crystalline solid (1.586 g).

LCMS (Method B): Rt=1.00 min, MH$^+$ 483

Intermediate 15: 1,1-Dimethylethyl (3R)-3-fluoro-3-{[(7-{1-[(methyloxy)methyl]-1H-pyrazol-4-yl}-1,6-naphthyridin-5-yl)amino]methyl}-1-piperidinecarboxylate

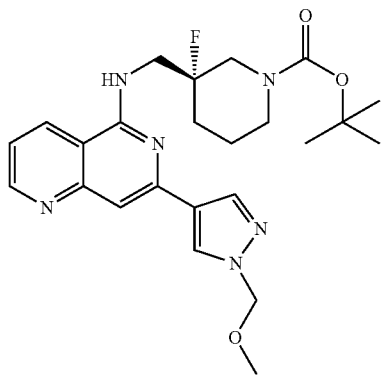 [SMILES: COCn1cc(-c2cc3ncccc3c(NC[C@]3(F)CCCN(C(=O)OC(C)(C)C)C3)n2)cn1]

To 1,1-dimethylethyl (3R)-3-{[(7-chloro-1,6-naphthyridin-5-yl)amino]methyl}-3-fluoro-1-piperidinecarboxylate (650 mg, 1.646 mmol) in DME (5 ml), water (2.5 ml), ethanol (5.00 ml) was added 1-[(methyloxy)methyl]-4-(4,4,5,5-tetramethyl-1,3,2-dioxaborolan-2-yl)-1H-pyrazole (1.03 g 4.33 mmol), potassium hydroxide (3.95 ml, 3.95 mmol, 1M aqueous solution) and PEPPSI (112 mg, 0.165 mmol). The reaction was refluxed at 130° C. under nitrogen for 4 nights. LCMS showed main peak as product. The reaction mixture was filtered through celite and the solvent removed. The residue was dissolved in DCM and loaded onto a 25 g silica column and purified on the SP4 eluting with a 50-100% ethyl acetate in cyclohexane gradient. Appropriate fractions were combined and the solvent removed to give a yellow oil which was dried under high vacuum overnight to give the title compound as a yellow solid/film (813 mg).

LCMS (Method B): Rt=0.86 min, MH$^+$ 471

Intermediate 16: 1,1-Dimethylethyl (3S)-3-{[(7-chloro-1,6-naphthyridin-5-yl)oxy]methyl}-3-fluoro-1-piperidinecarboxylate

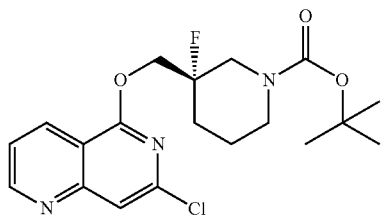 [SMILES: CC(C)(C)OC(=O)N1CCC[C@@](F)(COc2nc(Cl)cc3ncccc23)C1]

To an ice cooled solution of 1,1-dimethylethyl (3S)-3-fluoro-3-(hydroxymethyl)-1-piperidinecarboxylate (1.406 g, 6.03 mmol) in DMF (20 ml) was added sodium hydride (0.313 g, 7.84 mmol) (60% dispersion in mineral oil). This was stirred for 15 min before adding 5,7-dichloro-1,6-naphthyridine (1.2 g, 6.03 mmol). This was warmed to room temp and stirred for 4 h. The reaction had gone to completion and so was cautiously quenched with aqueous ammonium chloride before partitioning between aqueous ammonium chloride and ethyl acetate. The layers were separated and the aqueous was re-extracted with ethyl acetate. The combined organics were washed with brine and concentrated in vacuo to give the crude product. This was dissolved in DCM and purified through silica (50 g), eluting with a gradient of 0-50% ethyl acetate in DCM. Appropriate fractions were concentrated in vacuo to yield the title compound as a cream foamy gum (1.91 g).

LCMS: Rt=1.18 min, MH$^+$=395.85

Intermediate 17: 1,1-Dimethylethyl (3S)-3-({[7-(1-ethyl-1H-pyrazol-4-yl)-1,6-naphthyridin-5-yl]oxy}methyl)-3-fluoro-1-piperidinecarboxylate

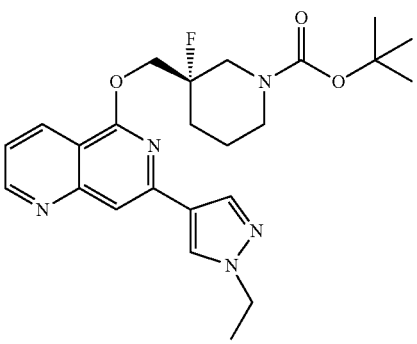 [SMILES: CCn1cc(-c2cc3ncccc3c(OC[C@]3(F)CCCN(C(=O)OC(C)(C)C)C3)n2)cn1]

A mixture of 1,1-dimethylethyl (3S)-3-{[(7-chloro-1,6-naphthyridin-5-yl)oxy]methyl}-3-fluoro-1-piperidinecarboxylate (1.1 g, 2.78 mmol), 1-ethyl-4-(4,4,5,5-tetramethyl-1,3,2-dioxaborolan-2-yl)-1H-pyrazole (0.679 g, 3.06 mmol) and caesium carbonate (2.263 g, 6.95 mmol) in 1,4-dioxane (16 ml) and water (3 ml) was degassed with nitrogen before adding tetrakis(triphenylphosphine)palladium (0) (0.096 g, 0.083 mmol). This was heated under reflux for 18 h. The reaction was partitioned between ethyl acetate and aqueous ammonium chloride. The aqueous was re-extracted with ethyl acetate and the combined organics were washed with brine, passed through a hydrophobic frit and concentrated in vacuo to give crude product. This was dissolved in DCM and purified through silica (20 g) eluting with a gradient of ethyl acetate in DCM. The product eluted in neat ethyl acetate. Appropriate fractions were combined and concentrated in vacuo to yield the title compound as a pinkish cream foam (1.10 g).

LCMS: Rt=1.21 min, MH$^+$=456.09

Example 1

7-(1-Ethyl-1H-pyrazol-4-yl)-N-{[(3S)-3-fluoro-3-piperidinyl]methyl}-1,6-naphthyridin-5-amine

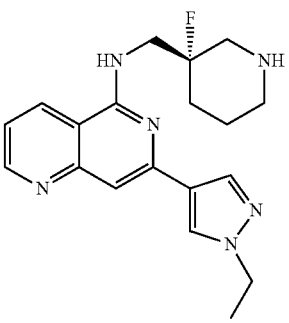 [SMILES: CCn1cc(-c2cc3ncccc3c(NC[C@]3(F)CCCNC3)n2)cn1]

To a solution of 1,1-dimethylethyl (3R)-3-({[7-(1-ethyl-1H-pyrazol-4-yl)-1,6-naphthyridin-5-yl]amino}methyl)-3-fluoro-1-piperidinecarboxylate (811 mg, 1.784 mmol) in DCM (6.1 ml) was added trifluoroacetic acid (3.16 ml, 41.0 mmol) and this was stirred at ambient temperature for 2 h. After this time the reaction had gone to completion and so was concentrated in vacuo to yield the crude product. This was dissolved in methanol and loaded onto an SCX cartridge (70 g) and eluted with methanol (3 column volumes) and 2M ammonia in methanol.

The filtrate from the ammonia fractions was concentrated in vacuo to give a yellow oil (653 mg). The free base (553 mg) was purified by High pH preparative MDAP (Method A). The appropriate vials were combined and concentrated in vacuo to afford the title compound as a yellow solid (265 mg).

$^1$H NMR (d6-DMSO) 8.65 ppm (1H, dd, CH), 8.70 ppm (1H, br.d, CH), 8.33 ppm (1H, s, CH), 8.05 ppm (1H, s, CH), 7.77 ppm (1H, br.t, NH), 7.37 ppm (1H, dd, CH), 7.25 ppm (1H, s, CH), 4.19 ppm (2H, q, $CH_2$), 3.95 ppm (2H, m, $CH_2$), 2.85-2.50 ppm (4H, 3×m, 2×$CH_2$), 1.90-1.54 ppm (4H, 2×m, 2×$CH_2$), 1.42 ppm (3H, t, $CH_3$).

HPLC (column: Luna 3u C18(2), #409663-12, 8-minute run time at 1 ml/min, eluent: 0-95% gradient of 0.05% TFA/Acetonitrile in 0.05% TFA/Water, wavelength 220 nm): Rt=2.49 min Optical rotation=−25.9 (c. 1.1 in methanol, T=23.6 C)

Preparation of the HCl Salt:

100 mg of the free base was dissolved in DCM (1 ml) and to this was added HCl (1.0M in $Et_2O$) (0.357 mL, 0.357 mmol). An orange solid immediately precipitated. The residual solvents were blown off and the resultant orange solid dried in vacuo to afford the title compound as the HCl salt (120 mg), as an orange solid.

LCMS (Method B): Rt=0.45 min, MH$^+$ 355

Example 2

7-[1-(1,1-Dimethylethyl)-1H-pyrazol-4-yl]-N-{[(3S)-3-fluoro-3-piperidinyl]methyl}-1,6-naphthyridin-5-amine

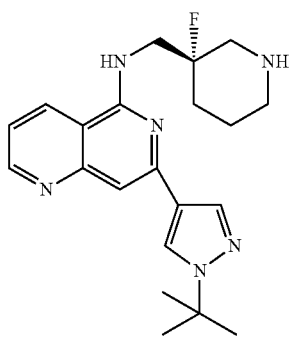 [SMILES: CC(C)(C)n1cc(-c2cc3ncccc3c(NC[C@]3(F)CCCNC3)n2)cn1]

1,1-Dimethylethyl (3R)-3-[({7-[1-(1,1-dimethylethyl)-1H-pyrazol-4-yl]-1,6-naphthyridin-5-yl}amino)methyl]-3-fluoro-1-piperidinecarboxylate (1.586 g, 3.29 mmol) was dissolved in DCM (5 ml) and trifluoroacetic acid (5.06 ml, 65.7 mmol) was added. The reaction was stirred for 20 min at 20° C. LCMS showed main peak of product. The reaction mixture was loaded onto a 20 g SCX cartridge and washed with methanol. The compound was eluted with 2M methanolic ammonia. The solvent from the ammonia fractions was evaporated and was kept under high vacuum for 2 h to give a yellow crystalline solid (1.171 g). The free base (1.12 g) was purified by High pH preparative MDAP (Method B). The appropriate fractions were combined, concentrated in vacuo and kept on high vacuum overnight to give the title compound as a yellow crystalline solid (688.1 mg).

LCMS (Method B): Rt=0.52 min, MH$^+$ 383

$^1$H NMR (MeOD) 8.80 ppm (1H, dd, CH), 8.58 ppm (1H, dd, CH), 8.32 ppm (1H, s, CH), 8.08 ppm (1H, s, CH), 7.39 ppm (1H, dd, CH), 7.25 ppm (1H, s, CH), 4.24 ppm (1H, dd, CH), 3.82 ppm (1H, dd, CH), 2.95-2.63 ppm (4H, 2×m, 2×$CH_2$), 2.00-1.69 ppm (4H, 3×m, 2×$CH_2$), 1.65 ppm (9H, s, 3×$CH_3$).

Preparation of the HCl Salt:

50 mg of the free base was dissolved in dichloromethane (DCM) (1 ml) and to this was added HCl (1.0M in $Et_2O$) (0.13 ml). The solvents were blown down overnight and the resulting product was dried in vacuo for 1 h to give the title compound as the HCl salt (56.6 mg), as an orange solid.

LCMS (Method B): Rt=0.53 min, MH$^+$ 383

Example 2

7-[1-(1,1-Dimethylethyl)-1H-pyrazol-4-yl]-N-{[(3S)-3-fluoro-3-piperidinyl]methyl}-1,6-naphthyridin-5-amine—Alternative Preparation To a solution of 1,1-dimethylethyl (3R)-3-[({7-[1-(1,1-dimethylethyl)-1H-pyrazol-4-yl]-1,6-naphthyridin-5-yl}amino)methyl]-3-fluoro-1-piperidinecarboxylate (2.24 g, 4.64 mmol) in DCM (14 ml) was added TFA (8.22 ml, 107 mmol) and this was stirred at ambient temperature for 2 h. After this time the reaction had gone to completion and so was concentrated in vacuo to yield the crude product. This was dissolved in methanol and loaded onto an SCX cartridge (50 g). It was eluted with methanol (3 CVs) and product eluted as the free base with 2M ammonia in methanol. The filtrate from the ammonia fractions was concentrated in vacuo to yield a yellow foam (1.55 g).

A portion of this (305 mg) was further purified by high pH MDAP to afford the title compound (265 mg)

LCMS (Method C): Rt=0.56 min, MH$^+$ 383

Optical rotation=−34.2 (c. 1.01 in methanol, T=23.6° C.).

Example 3

N-{[(3S)-3-Fluoro-3-piperidinyl]methyl}-7-{1-[(methyloxy)methyl]-1H-pyrazol-4-yl}-1,6-naphthyridin-5-amine

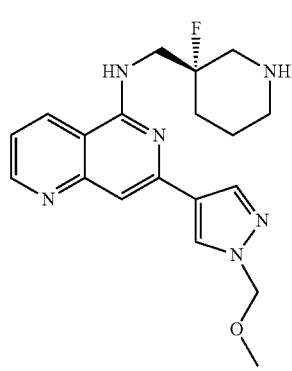 [SMILES: COCn1cc(-c2cc3ncccc3c(NC[C@]3(F)CCCNC3)n2)cn1]

To 1,1-dimethylethyl (3R)-3-fluoro-3-{[(7-{1-[(methyloxy)methyl]-1H-pyrazol-4-yl}-1,6-naphthyridin-5-yl)amino]methyl}-1-piperidinecarboxylate (813 mg, 1.728 mmol) in DCM (10 ml) was added trifluoroacetic acid (2 ml, 26.0 mmol) and stirred at room temperature for 2 h. LCMS showed product as the main peak. The solvent was removed and dissolved in methanol and loaded onto a pre-equilibrated 50 g SCX cartridge. Washed with methanol and eluted with 2M methanolic ammonia. The solvent from the ammonia fractions was removed and the residue dried under high vacuum overnight. The residue was purified on the large scale high pH MDAP (Method D). Appropriate fractions were combined and the solvent removed. The resulting product was dried under high vacuum for 1 h to give the title compound as a yellow solid (349 mg).

LCMS (Method B): Rt=0.43 min, MH+ 371

$^1$H NMR (MeOD) 8.84 ppm (1H, br.d, CH), 8.60 ppm (1H, br.d, CH), 8.44 ppm (1H, s, CH), 8.18 ppm, (1H, s, CH), 7.44 ppm (1H, dd, CH), 7.31 ppm (1H, s, CH), 5.49 ppm (2H, s, CH$_2$), 4.25-3.87 ppm (2H, 2×dd, CH$_2$), 3.38 ppm (3H, s, CH$_3$), 3.21-2.75 ppm (4H, 3×m, 2×CH$_2$), 2.10-1.75 ppm (4H, 2×m, 2×CH$_2$).

Optical rotation=−27.7 (c. 0.74 in methanol, T=23.6° C.)

Preparation of the HCl Salt:

47 mg of the free base was dissolved in dichloromethane (DCM) (1 ml) and a small amount of methanol and HCl (1.0M in Et$_2$O) (0.127 mL, 1 eq) was added. The solvent was removed and the residue was dried under high vacuum overnight to give the title compound as the HCl salt (48.5 mg), as a pale orange/yellow solid LCMS (Method B): Rt=0.43 min, MH+ 371

Example 4

7-(1-Ethyl-1H-pyrazol-4-yl)-5-({[(3S)-3-fluoro-3-piperidinyl]methyl}oxy)-1,6-naphthyridine

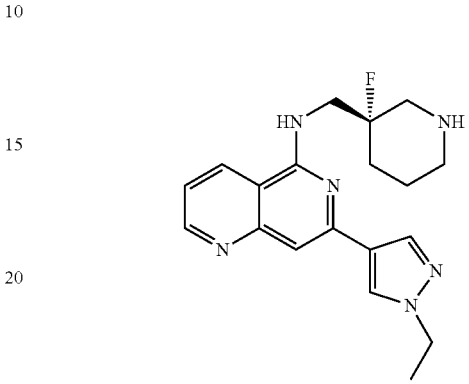

To a solution of 1,1-dimethylethyl (3S)-3-({[7-(1-ethyl-1H-pyrazol-4-yl)-1,6-naphthyridin-5-yl]oxy}methyl)-3-fluoro-1-piperidinecarboxylate (1.1 g, 2.415 mmol) in DCM (3 ml) was added trifluoroacetic acid (3 ml, 38.9 mmol) and this was stirred at room temp for 3 h. The reaction had gone to completion and so was concentrated in vacuo to yield the crude product. The TFA salt was dissolved in methanol and loaded onto an SCX cartridge (20 g). The impurities were eluted with methanol, and the product was eluted with 2M ammonia in methanol. The filtrate was concentrated in vacuo to yield a cream gummy solid (620 mg). This was purified by large-scale MDAP (Method C). The appropriate vials were combined and concentrated in vacuo to give the product as the TFA salt. To form the free base, this was dissolved in methanol and purified through an SCX cartridge (20 g) eluting with methanol. The product was eluted with 2M ammonia in methanol. The filtrate was concentrated in vacuo to yield the title compound as a clear glass (500 mg).

LCMS (Method C): Rt=0.51 min, MH+=355.9

$^1$H NMR (MeOD) 8.92 ppm (1H, dd, CH), 8.57 ppm (1H, br.d, CH), 8.30 ppm (1H, s, CH), 8.10 ppm (1H, s, CH), 7.58 ppm (1H, s, CH), 7.51 ppm (1H, dd, CH), 4.68 ppm (2H, m, CH$_2$), 4.26 ppm (2H, q, CH$_2$), 3.30-2.60 ppm (4H, 3×m, 2×CH$_2$), 2.20-1.62 ppm (4H, 3×m, 2×CH$_2$), 1.52 ppm (3H, t, CH$_3$).

Optical rotation=−7.6 (c. 0.79 in methanol, T=23.6° C.)

Preparation of the HCl Salt:

115 mg of the free base was dissolved in DCM (2 ml) and to this was added 1M HCl in diethyl ether (0.32 ml). This was blown down under nitrogen and dried in vacuo to yield the title compound as the HCl salt (74 mg), as a cream solid.

LCMS (Method C): Rt=0.51 min, MH+=356

Examples 5 to 11

The following further examples were similarly prepared:

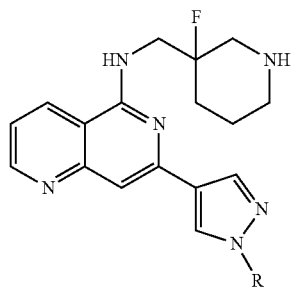

| Name | R— | Alkylating agent§ to form boronic ester | Stereo-chemistry | LCMS MH+ | LCMS Rt (min) |
|---|---|---|---|---|---|
| Ex 5: 1-{4-[5-({[(3S)-3-fluoro-3-piperidinyl]methyl}amino)-1,6-naphthyridin-7-yl]-1H-pyrazol-1-yl}-2-methyl-2-propanol | —CH$_2$C(Me)$_2$OH | (epoxide, 2,2-dimethyloxirane) | homochiral | 399 | 0.42 (Method B) |
| Ex 6: 2-{4-[5-({[(3S)-3-fluoro-3-piperidinyl]methyl}amino)-1,6-naphthyridin-7-yl]-1H-pyrazol-1-yl}ethanol | —CH$_2$CH$_2$OH | (ethylene carbonate) | homochiral | 371 | 0.38 (Method B) |
| Ex 7: N-{[(3S)-3-fluoro-3-piperidinyl]methyl}-7-{1-[2-(methyloxy)ethyl]-1H-pyrazol-4-yl}-1,6-naphthyridin-5-amine | —CH$_2$CH$_2$OMe | MeO–CH$_2$CH$_2$–Br | homochiral | 385 | 0.43 (Method B) |
| Ex 8: 7-(1-cyclopentyl-1H-pyrazol-4-yl)-N-[(3-fluoro-3-piperidinyl)methyl]-1,6-naphthyridin-5-amine | -cyclopentyl | cyclopentyl-Br | racemic | 395 | 0.59 (Method C) |
| Ex 9 Enantiomer A: N-{[3-fluoro-3-piperidinyl]methyl}-7-[1-(2,2,2-trifluoroethyl)-1H-pyrazol-4-yl]-1,6-naphthyridin-5-amine | —CH$_2$CF$_3$ | MsO–CH$_2$–CF$_3$ | homochiral | 409 | 0.50 (Method B) |
| Ex 9 Enantiomer B: N-{[3-fluoro-3-piperidinyl]methyl}-7-[1-(2,2,2-trifluoroethyl)-1H-pyrazol-4-yl]-1,6-naphthyridin-5-amine | —CH$_2$CF$_3$ | MsO–CH$_2$–CF$_3$ | homochiral | 409 | 0.51 (Method B) |
| Ex 10: N-[(3-fluoro-3-piperidinyl)methyl]-7-[1-(phenylmethyl)-1H-pyrazol-4-yl]-1,6-naphthyridin-5-amine | -benzyl | Not synthesised-boronic ester commercially available (Aldrich) | racemic | 417 | 0.6 (Method C) |
| Ex 11 Enantiomer A: N-{[3-fluoro-3-piperidinyl]methyl}-7-[1-(1-methylethyl)-1H-pyrazol-4-yl]-1,6-naphthyridin-5-amine | CH(Me)$_2$ | iPr-Br | homochiral | 369 | 0.46 (Method B) |
| Ex 11 Enantiomer B: N-{[3-fluoro-3-piperidinyl]methyl}-7-[1-(1-methylethyl)-1H-pyrazol-4-yl]-1,6-naphthyridin-5-amine | CH(Me)$_2$ | iPr-Br | homochiral | 369 | 0.47 (Method B) |

* Example 11 was prepared using an FMOC protected piperidine, rather than the BOC protected piperidine and separation of enantiomers at FMOC protected formula (I).
§Alkylating agents are commercially available from, for example, Sigma-Aldrich UK (Aldrich).

Process Description for Scheme 6

Stage a)

Preparation of (1S,2R,5S)-5-methyl-2-(1-methyl-ethyl)cyclohexyl 2-oxo-3-piperidinecarboxylate

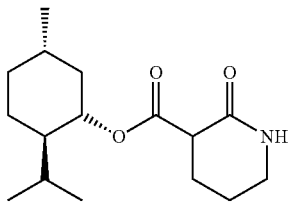

4-Dimethylaminopyridine (0.35 wt), (+)-menthol (0.95 wt) and ethyl 2-oxo-3-piperidinecarboxylate (1 wt) are dissolved/suspended in toluene (10 vol). The mixture is heated to reflux and stirred for seven days with periodic distillation of solvent and replenishment with fresh toluene. The reaction mixture is cooled to 25° C. and washed with two portions of 5% w/w aqueous HCl (4 vol) and then water (4 vol). The organic phase is concentrated under reduced pressure to give the title compound as a colourless oil.

Preparation of [(S)-2,2'-bis(diphenylphosphino)-1,1'-binaphtyl]bis(acetonitrile)palladium(II)ditriflate, catalyst for stage b)

Palladium acetate (1 wt) is dissolved in acetonitrile (4 vol) and stirred at 20±3° C. for 1 h. The reaction mixture is cooled to 0±3° C. and trifluoromethanesulfonic acid (0.75 vol, 1.9 eq) is added slowly over 30 min. After stirring for 15 min at 0±3° C. the reaction mixture is heated to 20±3° C. and stirred for a further 30 min. (S)-BINAP (2.77 wt, 1 eq) is added followed by a wash of acetonitrile (0.6 vol) and the mixture is stirred at 20±3° C. for 2.5 h. Diisopropyl ether (10 vol) is added slowly to give a slurry which is aged for 30 min. The solid is filtered off under suction and washed with acetonitrile:diisopropyl ether (1:3, 8 vol) and diisopropyl ether (8 vol). The product is then dried in vacuo at 20±3° C. to constant probe temperature.

Stage b)

Preparation of (1S,2R,5S)-5-methyl-2-(1-methyl-ethyl)cyclohexyl(3S)-3-fluoro-2-oxo-3-piperidinecarboxylate

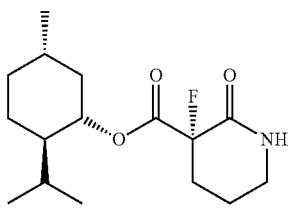

(1S,2R,5S)-5-Methyl-2-(1-methylethyl)cyclohexyl 2-oxo-3-piperidinecarboxylate (1 wt) is dissolved in ethanol (1.5 vol) and N-fluorobenzenesulfonimide (NFSI) (1.07 wt) added, followed by [(S)-BINAP]Pd(CH₃CN)₂(OTf)₂ (0.038 wt) at 20° C. Residual NFSI and catalyst were washed in with ethanol (3 vol). The jacket is cooled to 0° C. and 2,6-lutidine (0.21 vol) charged slowly, maintaining the temperature below 20° C. The jacket temperature is then raised to 20° C. The reaction mixture is stirred for 24 h, cooled to 0° C. and stirred for an additional 2 h. The solids are isolated by filtration, washing with ethanol (3 vol) and dried under vacuum at 40° C. The dried crude solid is charged to a reactor, and dichloromethane (5 vol) added. The dichloromethane phase is washed sequentially with 2M aqueous NaOH (3 vol), water (3 vol), 5% w/w aqueous HCl (3 vol) and water (3 vol). The dichloromethane extract is transferred to a rotary evaporator and solvent swapped with n-heptane under reduced pressure to give a mobile slurry and a final volume of ca 11 vol. The product is isolated by filtration, washed with heptane (3 vol) and dried under vacuum at 40° C.

Stage c)

Preparation of 1,1-dimethylethyl (3S)-3-fluoro-3-(hydroxymethyl)-1-piperidinecarboxylate

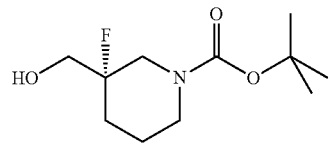 [SMILES: CC(C)(C)OC(=O)N1CCC[C@@](F)(CO)C1]

(1S,2R,5S)-5-Methyl-2-(1-methylethyl)cyclohexyl (3S)-3-fluoro-2-oxo-3-piperidinecarboxylate (1 eq, 1 wt) is suspended in anhydrous THF (6 vol) and treated with borane dimethyl sulfide complex (6 eq, 1.9 vol). The resulting solution is stirred at 63-66° C. for 40-46 h. The reaction mixture is cooled to 0±5° C. and slowly added to cold (0±5° C.) methanol (3 vol) over 30-90 min, maintaining the internal temperature below 15° C. Vigorous gas evolution and foaming is observed. 2M Hydrochloric acid (4 vol) is added over 10-15 min, maintaining the internal temperature below 15° C. The mixture is stirred at reflux (60-65° C.) for 30-90 min then cooled to 20-25° C. Toluene (4 vol) is added, the mixture stirred for 15 min then filtered. The filtrate is separated and the lower acidic aqueous phase run off. The filter cake is washed with 2M hydrochloric acid (2 vol) and the wash used for a second extraction of the toluene phase. The lower acidic aqueous phase is run off, combined with the first acidic aqueous and cooled to 5±5° C. The solution is treated with sodium hydroxide (5 eq, 0.668 wt) and stirred at 10-20° C. until the solid dissolved. A solution of di-tert-butyl-dicarbonate (1.1 eq, 0.802 wt) in dichloromethane (2 vol) is added and rinsed in with more dichloromethane (2 vol). The two-phase mixture is stirred vigorously for 15 h, filtered and the filter cake washed with dichloromethane (2 vol). The lower organic phase is run off. The filter cake is washed with dichloromethane (2 vol) and this wash used to extract the aqueous phase. The dichloromethane extracts are washed with water (4 vol) and concentrated in vacuo. The residual oil is dried on the Buchi at 40° C. Heptane (4 vol) is added and the mixture concentrated in vacuo. Towards the end of the evaporation the mixture is seeded with the title compound (0.001 wt), the resultant slurry concentrated to a small volume and diluted with heptane (4 vol). The slurry is rotated on Buchi at 40° C. for 20-36 min, cooled and rotated at 20±5° C. for 1 h. The solid is collected under suction, washed with heptane (2×1 vol) and dried in vacuo at 35±5° C.

Stage d)

Preparation of 1,1-dimethylethyl (3S)-3-fluoro-3-({[(trifluoromethyl)sulfonyl]oxy}methyl)-1-piperidinecarboxylate

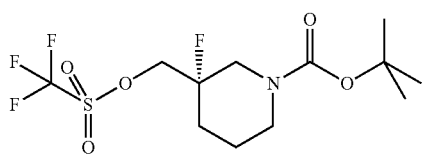 [SMILES: CC(C)(C)OC(=O)N1CCC[C@@](F)(COS(=O)(=O)C(F)(F)F)C1]

1,1-Dimethylethyl (3S)-3-fluoro-3-(hydroxymethyl)-1-piperidinecarboxylate (1 wt) in pyridine (3 vol) is dissolved at 20° C. under a nitrogen atmosphere. The resulting solution is cooled to −10° C., then triflic anhydride (0.80 vol) is added at such a rate as to maintain the internal temperature below 5° C. The reaction mixture is stirred at −10° C. for 4 h, then monitored for completion by TLC. The batch is warmed to 0° C., isopropyl acetate (8 vol) is added, followed by a solution of aqueous citric acid (5.8 wt citric acid in 5.8 vol of water). The mixture is stirred at 20° C. for 15 min, then the layers are separated. The organic layer is washed sequentially at 20° C. with another solution of aqueous citric acid (5.8 wt citric acid in 5.8 vol of water), followed by aqueous sodium bicarbonate solution (0.35 wt NaHCO$_3$ in water 4.65 vol) and water (5 vol). The organic phase is evaporated to dryness on a rotary evaporator to give the title compound as an orange oil.

Stage e)

Preparation of 1,1-dimethylethyl (3S)-3-(azidomethyl)-3-fluoro-1-piperidinecarboxylate

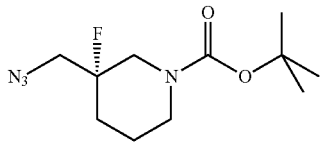 [SMILES: CC(C)(C)OC(=O)N1CCC[C@@](F)(CN=[N+]=[N-])C1]

1,1-Dimethylethyl (3S)-3-fluoro-3-({[(trifluoromethyl)sulfonyl]oxy}methyl)-1-piperidinecarboxylate (1 wt) is dissolved in N,N,-dimethylformamide (3 vol) at 20° C. and sodium azide (1.1 eq, 0.20 wt) is added. The resulting suspension is stirred at 20-30° C. for 6 h. TBME (5 vol) and water (9 vol) are added. The mixture is stirred for 5 min and the layers are separated. The aqueous phase is extracted with TBME (5 vol) and the TBME phases are combined. The combined organics are washed with water (2×5 vol), filtered and concentrated under reduced pressure to give the title compound as an orange oil.

Stage f)

Preparation of 1,1-dimethylethyl (3R)-3-(aminomethyl)-3-fluoro-1-piperidinecarboxylate

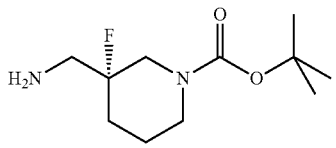 [SMILES: CC(C)(C)OC(=O)N1CCC[C@@](F)(CN)C1]

The hydrogenation vessel is purged with nitrogen. 1,1-Dimethylethyl (3S)-3-(azidomethyl)-3-fluoro-1-piperidinecarboxylate (1 wt) is dissolved in THF (11 vol) and charged to the vessel, rinsing in with THF (2 vol). Concentrated aqueous ammonia solution (~33% wt solution, 2 vol) is added, followed by 10% platinum on carbon (Johnson Matthey type 128; ~50% wet, 8.3% wt). The vessel is evacuated and purged with nitrogen 3 times. The reaction vessel is purged with hydrogen, stirring is started and hydrogenation carried out at atmospheric pressure maintaining an internal temperature of 20° C. for 38.5 h (reaction complete by LCMS). The vessel is evacuated and purged with nitrogen three times, and the contents passed through a CUNO Zetacarbon filter (R55SP). The vessel is washed with THF (3 vol) and this is passed through the previously used filter. The combined organics are concentrated to dryness on the rotary evaporator.

Stage g)

Preparation of 1,1-dimethylethyl (3R)-3-{[(7-chloro-1,6-naphthyridin-5-yl)amino]methyl}-3-fluoro-1-piperidinecarboxylate

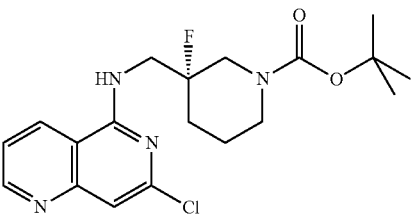 [SMILES: CC(C)(C)OC(=O)N1CCC[C@@](F)(CNc2nc(Cl)cc3ncccc23)C1]

A mixture of 5,7-dichloro-1,6-napthyridine (1 eq, 1 wt), 1,1-dimethylethyl (3R)-3-(aminomethyl)-3-fluoro-1-piperidinecarboxylate (1.1 eq, 1.28 wt), and diisopropylethylamine (2 eq, 1.75 vol) in NMP (6 vol) is stirred at 110±5° C. for 17 h. The solution is cooled to 70-75° C. and water (6 vol) added over 47 min at 65-75° C. The mixture is aged at 65-75° C. for 50 min, then cooled to 45° C. to give a slurry. The mixture is slowly cooled to 20-25° C. then aged for 2.25 h. The solid is collected under suction. The filter cake is washed with 1:2 v/v NMP/water (2 vol) then water (2×4 vol) and dried in vacuo at 40±5° C. As the solid still contains significant NMP (16.2% w/w) it is reslurried in 1:1 v/v NMP/water (7.3 vol). The slurry is heated to 65° C. and stirred at 65-66° C. for 1 h. The slurry is cooled to 20-25° C. and aged for 3 days. The solid is collected under suction. The filter cake is washed with 1:2 v/v NMP/water (2 vol) then water (2×4 vol) and dried in vacuo at 40±5° C.

Stages h) & i)

Preparation of 7-[1-(1,1-dimethylethyl)-1H-pyrazol-4-yl]-N-{[(3S)-3-fluoro-3-piperidinyl]methyl}-1,6-naphthyridin-5-amine dihydrochloride (Hydrochloride salt of Example 2)

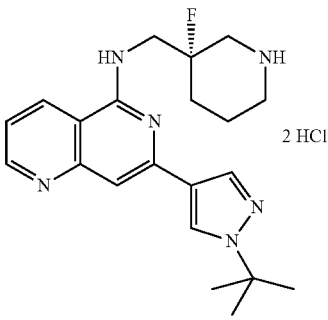 [SMILES: CC(C)(C)n1cc(-c2cc3ncccc3c(NC[C@]3(F)CCCNC3)n2)cn1]

1,1-Dimethylethyl (3R)-3-{[(7-chloro-1,6-naphthyridin-5-yl)amino]methyl}-3-fluoro-1-piperidinecarboxylate (1 wt), 1-(1,1-dimethylethyl)-4-(4,4,5,5-tetramethyl-1,3,2-dioxaborolan-2-yl)-1H-pyrazole (0.76 wt), sodium bicarbonate (0.64 wt) and 1,1'-bis(di-tert-butylphosphino)ferrocene palladium dichloride (0.00825 wt) are dissolved/suspended in 1,4-dioxane (8 vol) and water (2 vol). The mixture is heated to reflux and stirred for 3 h. The mixture is cooled to 20±3° C. to form a suspension. The solid is filtered off under vacuum. The filtrate is concentrated to 2 vol via vacuum distillation. Toluene (10 vol) is added. The solution is washed with water (5 vol) then stirred with Silicycle Si-Thiol derivatised silica gel (1 wt) at 60-65° C. for 2 h. The mixture is filtered at 60-65° C. and the cake washed with toluene (2 vol). The organic filtrate is then heated to 60-63° C. and 4M hydrogen chloride in 1,4-dioxane (2.9 vol) added over 30 min. The mixture is stirred at 60-63° C. for 5 h. The resulting slurry is cooled to 20±3° C. and aged for 15.5 h. The solid is filtered off under suction and washed with toluene (2×2 vol). The product is dried in vacuo at 40±3° C. to constant probe temperature.

Stage j)

Preparation of 7-[1-(1,1-dimethylethyl)-1H-pyrazol-4-yl]-N-{[(3S)-3-fluoro-3-piperidinyl]methyl}-1,6-naphthyridin-5-amine (Example 2)

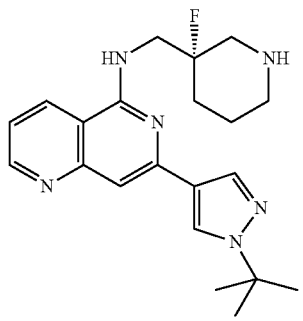 [SMILES: CC(C)(C)n1cc(-c2cc3ncccc3c(NC[C@]3(F)CCCNC3)n2)cn1]

7-[1-(1,1-Dimethylethyl)-1H-pyrazol-4-yl]-N-{[(3S)-3-fluoro-3-piperidinyl]methyl}-1,6-naphthyridin-5-amine dihydrochloride (1 wt) is dissolved/suspended in water (10 vol) and washed with ethyl acetate (2×5 vol). The acidic aqueous phase is basified with 32% NaOH (0.6 vol) to pH 10 and extracted with ethyl acetate (2×5 vol). The extracts are washed with 5% w/v sodium chloride in water (5 vol). The combined extracts are concentrated on the Buchi to a solid. The residue is suspended in n-butyl acetate (2.8 vol) and heated to 73-78° C. to complete dissolution. The solution is line filtered through a 5 µM domnick hunter filter, with a 0.2 vol line wash. The solution is cooled to 45-50° C. and seeded with the title compound (0.001 wt). The mixture is cooled to 40-45° C. and aged for 50 min. The slurry is diluted with TBME (3 vol) over 30 min at 40-45° C., and aged at 40-45° C. for 1 h. The slurry is cooled to 20-23° C. and aged for 16 h. The solid is filtered, washed with 1:1 v/v n-butyl acetate/TBME (1 vol) followed by TBME (2×2 vol) and dried in vacuo at 40±5° C. to constant probe temperature.

Process Description for Scheme 7

Stage a)

Preparation of 2-(2-ethoxy-2-oxoethyl)nicotinic acid and 2-(2-isopropoxy-2-oxoethyl)nicotinic acid

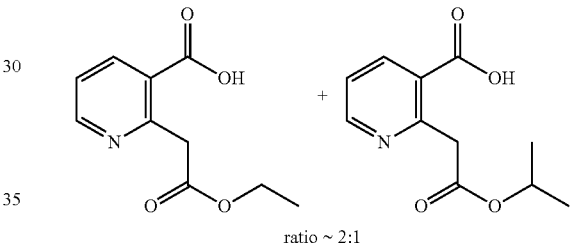

ratio ~ 2:1

The reactor is charged with potassium tert-butoxide (3 eq) followed by iso-propanol (9 vol) under nitrogen atmosphere at 30±5° C. The mixture is stirred to dissolve. After cooling to ~30° C., ethyl acetoacetate (2 eq) is slowly added under nitrogen atmosphere at <40° C. After stirring for 1-2 h copper acetate (0.1 eq) is charged at 35±5° C., followed by 2-chloronicotinic acid (1 eq). This is followed by a rinse of isopropyl alcohol (1 vol). The reaction mixture is heated to 78±3° C. under nitrogen atmosphere for at least 4 h then sampled. On receipt of a successful sample result the reaction is cooled to 30±5° C. and quenched with water, followed by dilute HCl to adjust the pH to 6-7.

The reaction mixture is concentrated by vacuum distillation at <50° C. to 4-5 volumes. 10% NaCl solution is added followed by ethyl acetate. Further dilute HCl is added to adjust the pH to 2.5-3.0. The biphasic mixture is then filtered through a celite bed and the cake washed with ethyl acetate (twice). The ethyl acetate and aqueous layers are separated then the aqueous layer back extracted with ethyl acetate (twice). The ethyl acetate phase is washed with water and 5% aq. NaCl solution. The organic phase is distilled to 1-2 volumes under vacuum at <50° C. Toluene is added and the mixture distilled again down to 1-2 volumes. This toluene addition/distillation step is repeated. The resulting toluene suspension is cooled to 30±5° C. and treated with hexane (10 vol). The suspension is stirred for 1-2 h at 30±5° C. then filtered. The solid is washed with hexane (2 vol) then off-loaded and dried at 52.5±2.5° C. under vacuum (NLT 650 mm of Hg) for 10 h.

Stages b) & c)

Preparation of 1,6-naphthyridin-5,7(6H,8H)-dione

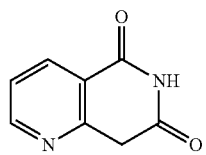 [SMILES: O=C1Cc2ncccc2C(=O)N1]

Tetrahydrofuran (9 vol) is charged to the reactor followed by the starting material ester (1 eq) and a rinse of tetrahydrofuran (1 vol). The mixture is cooled to −2.5±7.5° C. under nitrogen atmosphere then treated with triethylamine (1.35 eq) and later ethyl chloroformate (1.25 eq). The reaction is stirred for 1 h at −2.5±7.5° C. then sampled. On receipt of a successful result the reaction is carefully treated with aq. ammonia, stirred, then water is added. Dilute HCl is added at <5° C. to adjust the pH to 6.5-7.5. The mixture is distilled under vacuum at <40° C. to 12-14 volumes and cooled to 7.5±2.5° C. The suspension is stirred ~1 h at 7.5±2.5° C. then filtered. The solid is washed with water (1 vol) then offloaded and dried under vacuum (NLT 650 mm of Hg) at 52.5±2.5° C. for 12.0 h.

Stages d) & e)

Preparation of 5,7-Dichloro-1,6-napthyridine

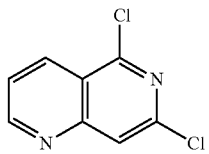

Phosphorus oxychloride (3 vol) is charged to the reactor at 30±5° C. followed by 1,6-naphthyridin-5,7(6H,8H)-dione (1 eq), tetramethylammonium chloride (1.05 eq) and a rinse of phosphorus oxychloride (0.5 vol). The mixture is heated to 103.5±3.5° C. and stirred for a minimum of 36 h. The reaction is then cooled to 60±5° C. and sampled. On receipt of a successful sample, toluene (4 vol) is added and the mixture concentrated to 2-3 volumes by distillation under vacuum (NLT 650 mm of Hg) and temperature<60° C. Additional toluene (2 vol) is added and again the mixture distilled under vacuum to 2-3 vols. This toluene addition/distillation cycle is repeated once more then the mixture is cooled to 47.5±2.5° C. and treated with tetrahydrofuran (8 vol) and ethyl acetate (8 vol). The mixture is cooled to 30±5° C. and poured into 15% aq. sodium carbonate (15 vol) which has been pre-cooled to 5.0±5.0° C. Additional tetrahydrofuran (3 vol) is added along with ethyl acetate (3 vol) in order to rinse out the initial reaction vessel. Whilst still at 5±5° C. the mixture is slowly treated with further 15% aqueous sodium carbonate solution (5 vol) and stirred for 15-30 min. The temperature is increased to 22.5±2.5° C. and the pH adjusted to 7-8 by addition of either 15% aqueous sodium carbonate solution or dilute HCl. Ethyl acetate (5 vol) is added followed by celite. The mixture is stirred then filtered. The celite bed is washed with ethyl acetate (2×2 vol). The filtrate is distilled at <55° C. under vacuum (NLT 650 mm of Hg) down to 30±5 volumes. Water (2 vol) is added and the distilled again down to ~30 vols. This water addition/distillation cycle is repeated until the tetrahydrofuran, toluene and ethyl acetate content are each NMT 3.0% by GC (% w/w). At that point, water (10 vol) is added and the mixture heated to 42.5±2.5° C. and stirred for 30-60 min. The product is isolated by filtration at 42.5±2.5° C. and washed with water (2×3 vol). The cake is sucked dry then offloaded and charged to a separate reactor. Water (20 vol) is added and the suspension heated to 42.5±2.5° C. and stirred for 30-60 min 42.5±2.5° C. The product is filtered and washed with water (2×3 vol), sucked dry then transferred to a vacuum oven and further dried at 52.5±2.5° C. under vacuum (NLT 650 mm of Hg) for 8±2 h.

Process Description for Scheme 8

Stage a)

Preparation of 1-(1,1-Dimethylethyl)-1H-pyrazole (Intermediate 9)

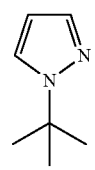

To a mixture of 1,1,3,3-tetramethoxypropane (3.82 kg, 23.27 mol) and tert-butylhydrazine hydrochloride (2.9 kg, 23.27 mol) in ethanol (24.54 kg), conc HCl (4.72 kg, 46.55 mol) was added, keeping the temperature below 50° C. The reaction mixture was then rapidly heated to reflux. After ca. 2 h the reaction was sampled and analysed by NMR. Pass criteria was <3.0% starting material remaining. On receipt of a pass result the solution is cooled, diluted with water (8.29 kg) and evaporated in vacuo (T<50° C., p<−0.08 MPa) until approximately all of the original ethanol was removed. The solution was basified with 10M NaOH(aq), extracted with EtOAc (11.11 kg×2) and the organic phase washed with saturated ammonium chloride solution (4.3 ml/g×2) and brine (4.3 ml/g), then evaporated to give the title compound (2.08 kg, 72% yield) as a brown liquid (GC purity 99.70% a/a).

Stage b)

Preparation of 4-Bromo-1-(1,1-dimethylethyl)-1H-pyrazole (Intermediate 10)

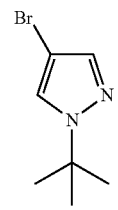

To an ice cooled solution (0° C. to 10° C.) of 1-(tert-butyl) pyrazole (1.75 kg, 14.09 mol) in dichloromethane (12.9 kg) was added NBS (2.63 kg, 14.79 mol) portionwise. The solu-

Stage c)

Preparation of iso-Propyl pinacol borate

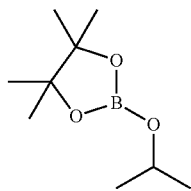

To a 20 L four-neck bottle tri-isopropyl borate (261.0 g, 1.388 mol) and pinacol (142.5 g, 1.207 mol) were added and heated to ~90° C. for 12-16 h. The criteria for a reaction completion is pinacol<4.0% by GC. After completion, the reaction was converted to distillation, and the product fractions (boiling at 174-178° C.) collected. Thus the title product was obtained as a colourless oil in a yield range of 80-90% th across the six 20 L batches which were operated. GC records purity of 87-96%, but $^1$H NMR shows the product to be very pure. [discrepancy due to product instability to GC conditions.]

Stage d)

Preparation of 1-(1,1-Dimethylethyl)-4-(4,4,5,5-tetramethyl-1,3,2-dioxaborolan-2-yl)-1H-pyrazole (Intermediate 11)

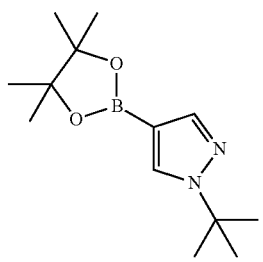 [SMILES: CC(C)(C)n1cc(B2OC(C)(C)C(C)(C)O2)cn1]

To a 20 L four-neck bottle, 4-bromo-(tert-butyl)pyrazole (1.15 kg, 5.66 mol) and THF (9.2 L) were added, then the mixture was cooled to between −78° C. and −85° C. and treated with nBuLi (6.23 mol) dropwise at that temperature. After addition the solution was stirred at the same temperature for 1 h and isopropyl pinacol borate (1.47 kg, 7.92 mol) was added dropwise. The reaction was complete after stirring for ~3 h (starting material<1.0% a/a by GC) then water (2.3 L) was added to quench the reaction; and the pH adjusted to 8-9 by addition of 3.45 kg 1M HCl. The aqueous phase was extracted with TBME (3.45 L×2), and the combined organic phase washed with 5% NaCl (3.45 L×2) and water (3.45 L) in sequence. The organic phase was evaporated to give the crude product. After subsequent recrystallization from heptanes the pure product was obtained as a white solid (GC purity 99.7% a/a) in a 63.5% th overall yield. (Two 20 L reactions were run, then combined in the heptane recrystallization).

The invention claimed is:

1. A compound of formula (I):

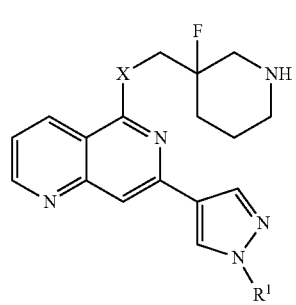

wherein:

X is O or NH;

$R^1$ is $C_{2-4}$ alkyl, $C_{3-7}$cycloalkyl, hydroxy$C_{2-4}$ alkyl, $C_{1-2}$ alkoxy$C_{1-4}$ alkyl, trifluoromethyl$C_{1-2}$ alkyl or benzyl; or a salt thereof.

2. A compound or a salt thereof according to claim 1 in which X is NH.

3. A compound or a salt thereof according to claim 1 in which $R^1$ is $C_{2-4}$ alkyl, $C_{3-7}$cycloalkyl or $C_{1-2}$alkoxy$C_{1-4}$ alkyl.

4. A compound or a salt thereof according to claim 1 in which $R^1$ is ethyl, t-butyl, —$CH_2OCH_3$, —$CH_2C(CH_3)_2OH$, —$CH_2CH_2OH$, —$CH_2CH_2OCH_3$, —$CH(CH_3)_2$, —$CH_2CF_3$, benzyl or cyclopentyl.

5. A compound or a salt thereof according to claim 4 in which $R^1$ is t-butyl.

6. A compound or a salt thereof selected from the group consisting of:

7-(1-ethyl-1H-pyrazol-4-yl)-N-{[(3S)-3-fluoro-3-piperidinyl]methyl}-1,6-naphthyridin-5-amine;

7-[1-(1,1-dimethylethyl)-1H-pyrazol-4-yl]-N-{[(3S)-3-fluoro-3-piperidinyl]methyl}-1,6-naphthyridin-5-amine;

N-{[(3S)-3-fluoro-3-piperidinyl]methyl}-7-{1-[(methyloxy)methyl]-1H-pyrazol-4-yl}-1,6-naphthyridin-5-amine;

7-(1-ethyl-1H-pyrazol-4-yl)-5-({[(3S)-3-fluoro-3-piperidinyl]methyl}oxy)-1,6-naphthyridine;

1-{4-[5-({[(3S)-3-fluoro-3-piperidinyl]methyl}amino)-1,6-naphthyridin-7-yl]-1H-pyrazol-1-yl}-2-methyl-2-propanol;

2-{4-[5-({[(3S)-3-fluoro-3-piperidinyl]methyl}amino)-1,6-naphthyridin-7-yl]-1H-pyrazol-1-yl}ethanol;

N-{[(3S)-3-fluoro-3-piperidinyl]methyl}-7-{1-[2-(methyloxy)ethyl]-1H-pyrazol-4-yl}-1,6-naphthyridin-5-amine;

7-(1-cyclopentyl-1H-pyrazol-4-yl)-N-[(3-fluoro-3-piperidinyl)methyl]-1,6-naphthyridin-5-amine;

N-[(3-fluoro-3-piperidinyl)methyl]-7-[1-(2,2,2-trifluoroethyl)-1H-pyrazol-4-yl]-1,6-naphthyridin-5-amine;

N-{[(3S)-3-fluoro-3-piperidinyl]methyl}-7-[1-(2,2,2-trifluoroethyl)-1H-pyrazol-4-yl]-1,6-naphthyridin-5-amine;

N-{[(3R)-3-fluoro-3-piperidinyl]methyl}-7-[1-(2,2,2-trifluoroethyl)-1H-pyrazol-4-yl]-1,6-naphthyridin-5-amine;

N-[(3-fluoro-3-piperidinyl)methyl]-7-[1-(phenylmethyl)-1H-pyrazol-4-yl]-1,6-naphthyridin-5-amine;

N-{[3-fluoro-3-piperidinyl]methyl}-7-[1-(1-methylethyl)-1H-pyrazol-4-yl]-1,6-naphthyridin-5-amine;

N-{[(3S)-3-fluoro-3-piperidinyl]methyl}-7-[1-(1-methylethyl)-1H-pyrazol-4-yl]-1,6-naphthyridin-5-amine; and N-{[(3R)-3-fluoro-3-piperidinyl]methyl}-7-[1-(1-methylethyl)-1H-pyrazol-4-yl]-1,6-naphthyridin-5-amine; and salts thereof.

7. A compound which is 7-[1-(1,1-dimethylethyl)-1H-pyrazol-4-yl]-N-{[(3S)-3-fluoro-3-piperidinyl]methyl}-1,6-naphthyridin-5-amine

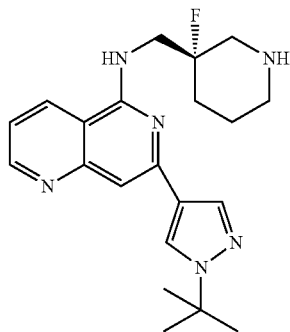 [SMILES: CC(C)(C)n1cc(-c2cc3ncccc3c(NC[C@]3(F)CCCNC3)n2)cn1]

or a salt thereof.

8. A compound or a salt thereof according to claim 1, wherein the salt is a pharmaceutically acceptable salt.

9. A pharmaceutical composition comprising a compound or a pharmaceutically acceptable salt thereof, as defined in claim 8 and one or more pharmaceutically acceptable excipients.

10. A method of treating an autoimmune condition, which comprises administering to a subject in need thereof a therapeutically effective amount of compound or a pharmaceutically acceptable salt thereof, as defined in claim 8, wherein the autoimmune condition is rheumatoid arthritis.

11. A method of treating chronic spontaneous urticaria, which comprises administering to a subject in need thereof a therapeutically effective amount of compound or a pharmaceutically acceptable salt thereof, as defined in claim 8.

* * * * *